United States Patent
Krawczyk et al.

(10) Patent No.: US 9,850,506 B2
(45) Date of Patent: Dec. 26, 2017

(54) MODIFIED MICROORGANISM FOR IMPROVED PRODUCTION OF FINE CHEMICALS ON SUCROSE

(71) Applicant: BASF SE, Ludwigshafen (DE)

(72) Inventors: Joanna Martyna Krawczyk, Mannheim (DE); Stefan Haefner, Speyer (DE); Hartwig Schröder, Nußloch (DE); Esther Dantas Costa, Mannheim (DE); Oskar Zelder, Speyer (DE); Gregory Von Abendroth, White Plains, NY (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/116,896

(22) PCT Filed: May 2, 2015

(86) PCT No.: PCT/EP2015/052380
§ 371 (c)(1),
(2) Date: Aug. 5, 2016

(87) PCT Pub. No.: WO2015/118051
PCT Pub. Date: Aug. 13, 2015

(65) Prior Publication Data
US 2017/0166937 A1    Jun. 15, 2017

(30) Foreign Application Priority Data
Feb. 7, 2014 (EP) ..................................... 14154288

(51) Int. Cl.
*C12P 7/46* (2006.01)
(52) U.S. Cl.
CPC ...................................... *C12P 7/46* (2013.01)
(58) Field of Classification Search
CPC ..................................................... C12N 1/20
USPC ............................................................. 435/145
See application file for complete search history.

(56) References Cited

U.S. PATENT DOCUMENTS

| | | |
|---|---|---|
| 2010/0159543 A1 | 6/2010 | Scholten et al. |
| 2013/0217087 A1 | 8/2013 | Lee et al. |

FOREIGN PATENT DOCUMENTS

| | | |
|---|---|---|
| WO | WO-2005/052135 A1 | 6/2005 |
| WO | WO-2007/019301 A2 | 2/2007 |
| WO | WO-2009/024294 A1 | 2/2009 |
| WO | WO-2010/092155 A1 | 8/2010 |
| WO | WO-2012/030130 A2 | 3/2012 |

OTHER PUBLICATIONS

Kilimann et al., Protection by sucrose against heat-induced lethal and sublethal injury of Lactococcus lactis: an FT-IR study, Biochim. Biophys. Acta, 1764(7):1188-97 (2006).
Kuhnert et al., *Basfia succiniciproducens* gen. nov., sp. nov., a new member of the family Pasteurellaceae isolated from bovine rumen, Int. J. Syst. Evol. Microbiol., 60(Pt. 1):44-50 (2010).
Lee et al., Mannheimia succiniciproducens phosphotransferase system for sucrose utilization, Appl. Environ. Microbiol., 76(5):1699-703 (2010).
Macfayden et al., Regulation of competence development and sugar utilization in Haemophilus influenzae Rd by a phosphoenolpyruvate:fructose phosphotransferase system, Mol. Microbiol., 21(5):941-52 (1996).
International Search Report and Written Opinion, International Application No. PCT/EP2015/052380, dated Jun. 22, 2015.
International Preliminary Report on Patentability (Chapter II), International Application No. PCT/EP2015/052380, dated Apr. 12, 2016.
European Search Report, European patent application No. 14154288, dated Apr. 8, 2014.

*Primary Examiner* — Tekchand Saidha
(74) *Attorney, Agent, or Firm* — Marshall, Gerstein & Borun LLP

(57) ABSTRACT

The present invention relates to a modified microorganism having, compared to its wild-type, a reduced activity of the enzyme that is encoded by the fruA-gene. The present invention also relates to a method for producing an organic compound and to the use of modified microorganisms.

7 Claims, 4 Drawing Sheets

SEQUENCE LISTING

<160> NUMBER OF SEQ ID NOS: 14

<210> SEQ ID NO 1
<211> LENGTH: 1517
<212> TYPE: DNA
<213> ORGANISM: Basfia succiniciproducens
<220> FEATURE:
<221> NAME/KEY: misc_feature
<222> LOCATION: (1)..(1517)
<223> OTHER INFORMATION: 16 S rDNA of strain DD1

<400> SEQUENCE: 1

```
tttgatcctg gctcagattg aacgctggcg gcaggcttaa cacatgcaag tcgaacggta      60
gcgggaggaa agcttgcttt ctttgccgac gagtggcgga cgggtgagta atgcttgggg     120
atctggctta tggaggggga taacgacggg aaactgtcgc taataccgcg taatatcttc     180
ggattaaagg gtgggacttt cgggccaccc gccataagat gagcccaagt gggattaggt     240
agttggtggg gtaaaggcct accaagccga cgatctctag ctggtctgag aggatgacca     300
gccacactgg aactgagaca cggtccagac tcctacggga ggcagcagtg gggaatattg     360
cacaatgggg ggaaccctga tgcagccatg ccgcgtgaat gaagaaggcc ttcgggttgt     420
aaagttcttt cggtgacgag gaaggtgttt gttttaatag acaagcaat tgacgttaat     480 cacagaagaa gcaccggcta actccgtgcc agcagccgcg gtaatacgga gggtgcgagc     540
gttaatcgga ataactgggc gtaaagggca tgcaggcgga ctttttaagtg agatgtgaaa     600 gccccgggct taacctggga attgcatttc agactgggag tctagagtac tttagggagg     660
ggtagaattc cacgtgtagc ggtgaaatgc gtagagatgt ggaggaatac cgaaggcgaa     720 ggcagccct tgggaagata ctgacgctca tatgcgaaag cgtggggagc aaacaggatt     780
agatacccct gtagtccacg cggtaaacgc tgtcgatttg gggattgggc tttaggcctg     840
gtgctcgtag ctaacgtgat aaatcgaccg cctgggagt acggccgcaa ggttaaaact     900
caaatgaatt gacggggcc cgcacaagcg gtggagcatg tggtttaatt cgatgcaacg     960
cgaagaacct tacctactct tgacatccag agaatcctgt agagatacgg gagtgccttc    1020
gggagctctg agacaggtgc tgcatggctg tcgtcagctc gtgttgtgaa atgttgggtt    1080
aagtcccgca acgagcgcaa cccttatcct ttgttgccag catgtaaaga tgggaactca    1140
aaggagactg ccggtgacaa accggaggaa ggtgggatg acgtcaagtc atcatggccc    1200
ttacgagtag ggctacacac gtgctacaat ggtgcataca gagggcggcg ataccgcgag    1260
gtagagcgaa tctcagaaag tgcatcgtag tccggattgg agtctgcaac tcgactccat    1320
gaagtcggaa tcgctagtaa tcgcaaatca gaatgttgcg gtgaatacgt tcccgggcct    1380
tgtacacacc gcccgtcaca ccatgggagt gggttgtacc agaagtagat agcttaacct    1440 tcggggggg cgtttaccac ggtatgattc atgactgggg tgaagtcgta acaaggtaac    1500 cgtagggaa cctgcgg                                                   1517
```

<210> SEQ ID NO 2
<211> LENGTH: 3008
<212> TYPE: DNA
<213> ORGANISM: Basfia succiniciproducens
<220> FEATURE:
<221> NAME/KEY: misc_feature
<222> LOCATION: (1)..(3008)
<223> OTHER INFORMATION: 23 S rDNA of strain DD1

<400> SEQUENCE: 2

```
agtaataacg aacgacacag gtataagaat acttgaggtt gtatggttaa gtgactaagc      60
```

```
gtacaaggtg gatgccttgg caatcagagg cgaagaagga cgtgctaatc tgcgaaaagc    120
ttgggtgagt tgataagaag cgtctaaccc aagatatccg aatggggcaa cccagtagat    180
gaagaatcta ctatcaataa ccgaatccat aggttattga ggcaaaccgg gagaactgaa    240
acatctaagt accccgagga aaagaaatca accgagatta cgtcagtagc ggcgagcgaa    300
agcgtaagag ccggcaagtg atagcatgag gattagagga atcggctggg aagccgggcg    360
gcacagggtg atagccccgt acttgaaaat cattgtgtgg tactgagctt gcagaagta    420 gggcgggaca cgagaaatcc tgtttgaaga aggggggacc atcctccaag gctaaatact    480
cctgattgac cgatagtgaa ccagtactgt gaaggaaagg cgaaaagaac cccggtgagg    540
ggagtgaaat agaacctgaa accttgtacg tacaagcagt gggagcccgc gagggtgact    600
gcgtaccttt tgtataatgg gtcagcgact tatattatgt agcgaggtta accgaatagg    660
ggagccgaag ggaaaccgag tcttaactgg gcgtcgagtt gcatgatata gacccgaaac    720
ccggtgatct agccatgggc aggttgaagg ttgggtaaca ctaactggag gaccgaaccg    780
actaatgttg aaaaattagc ggatgacctg tggctggggg tgaaaggcca atcaaaccgg    840
gagatagctg gttctccccg aaatctattt aggtagagcc ttatgtgaat accttcgggg    900
gtagagcact gtttcggcta gggggccatc ccggcttacc aacccgatgc aaactgcgaa    960
taccgaagag taatgcatag gagacacacg gcgggtgcta acgttcgtcg tggagaggga   1020
aacaacccag accgccagct aaggtcccaa agtttatatt aagtgggaaa cgaagtggga   1080
aggcttagac agctaggatg ttggcttaga agcagccatc atttaaagaa agcgtaatag   1140
ctcactagtc gagtcggcct gcgcggaaga tgtaacgggg ctcaaatata gcaccgaagc   1200
tgcggcatca ggcgtaagcc tgttgggtag gggagcgtcg tgtaagcgga agaaggtggt   1260
tcgagagggc tgctggacgt atcacgagtg cgaatgctga cataagtaac gataaaacgg   1320
gtgaaaaacc cgttcgccgg aagaccaagg gttcctgtcc aacgttaatc ggggcagggt   1380
gagtcggccc ctaaggcgag gctgaagagc gtagtcgatg ggaaacgggt taatattccc   1440
gtacttgtta taattgcgat gtggggacgg agtaggttag gttatcgacc tgttggaaaa   1500
ggtcgtttaa gttggtaggt ggagcgttta ggcaaatccg gacgcttatc aacaccgaga   1560
gatgatgacg aggcgctaag gtgccgaagt aaccgatacc acacttccag gaaaagccac   1620
taagcgtcag attataataa accgtactat aaaccgacac aggtggtcag gtagagaata   1680
ctcaggcgct tgagagaact cgggtgaagg aactaggcaa aatagcaccg taacttcggg   1740
agaaggtgcg ccggcgtaga ttgtagaggt atacccttga aggttgaacc ggtcgaagtg   1800
acccgctggc tgcaactgtt tattaaaaac acagcactct gcaaacacga aagtggacgt   1860 ataggtgtg atgcctgccc ggtgctgaa ggttaattga tggcgttatc gcaagagaag   1920
cgcctgatcg aagccccagt aaacggcggc cgtaactata cggtcctaa ggtagcgaaa   1980 ttccttgtcg ggtaagttcc gacctgcacg aatggcataa tgatggccag gctgtctcca   2040
cccgagactc agtgaaattg aaatcgccgt gaagatgcgg tgtacccgcg gctagacgga   2100
aagaccccgt gaacctttac tatagcttga cactgaacct tgaattttga tgtgtaggat   2160
aggtgggagg ctttgaagcg gtaacgccag ttatcgtgga gccatccttg aaataccacc   2220
ctttaacgtt tgatgttcta acgaagtgcc cggaacgggt actcggacag tgtctggtgg   2280
gtagtttgac tggggcggtc tcctcccaaa gagtaacgga ggagcacgaa ggtttgctaa   2340
tgacggtcgg acatcgtcag gttagtgcaa tggtataagc aagcttaact gcgagacgga   2400
```

| | |
|---|---|
| caagtcgagc aggtgcgaaa gcaggtcata gtgatccggt ggttctgaat ggaagggcca | 2460 |
| tcgctcaacg gataaaaggt actccgggga taacaggctg ataccgccca agagttcata | 2520 |
| tcgacggcgg tgtttggcac ctcgatgtcg gctcatcaca tcctggggct gaagtaggtc | 2580 |
| ccaagggtat ggctgttcgc catttaaagt ggtacgcgag ctgggtttaa acgtcgtga | 2640 |
| gacagtttgg tccctatctg ccgtgggcgt tggagaattg agaggggctg ctcctagtac | 2700 |
| gagaggaccg gagtggacgc atcactggtg ttccggttgt gtcgccagac gcattgccgg | 2760 |
| gtagctacat gcggaagaga taagtgctga aagcatctaa gcacgaaact tgcctcgaga | 2820 |
| tgagttctcc cagtatttaa tactgtaagg gttgttggag acgacgacgt agataggccg | 2880 |
| ggtgtgtaag cgttgcgaga cgttgagcta accggtacta attgcccgag aggcttagcc | 2940 |
| atacaacgct caagtgtttt tggtagtgaa agttattacg gaataagtaa gtagtcaggg | 3000 |
| aatcggct | 3008 |

<210> SEQ ID NO 3
<211> LENGTH: 1695
<212> TYPE: DNA
<213> ORGANISM: Basfia succiniciproducens
<220> FEATURE:
<221> NAME/KEY: misc_feature
<222> LOCATION: (1)..(1581)
<223> OTHER INFORMATION: nucleotide sequence of fruA-gene from strain DD1

<400> SEQUENCE: 3

| | |
|---|---|
| ttgaaggata agccgatgaa tatttttctt acgcaatcac caaatttagg tcgtgcaaaa | 60 |
| gcgtttttat tgcaccaggt tttggctgcc gcagtaaaac aacaaaatca tcaactggta | 120 |
| gaaaatgccg aacaagcgga tttagcgatt gttttcggta aactttgcc gaatttgacc | 180 |
| gcacttttag gtaaaaaagt gtatttggcg gatgaagaac aagcgttgaa tgcgcctgaa | 240 |
| aataccgtcg cgcaggcatt aaccgaggct gtggattatg ttcaaccggc gcaacaggac | 300 |
| gtgcaacccg caactgcttc cggtatgaaa aatatcgtgg cggttaccgc ttgtccgacc | 360 |
| ggggtggcgc acacctttat gtctgccgag gcgattacaa cctactgcca acagcaaggt | 420 |
| tggaatgtaa aagtggaaac cagaggtcaa gtcggtgcga caatatttat ttctgcggaa | 480 |
| gatgtggcgg cggccgattt agtctttatc gctacggata ttaatgtgga tttaagcaaa | 540 |
| ttcaaaggaa aaccgatgta tcgtacttca acgggcttag cattgaagaa aaccgcacag | 600 |
| gaatttgata agcctttaa agaagcgacg atttatcagg gtgaagaaac tacaaccacc | 660 |
| acagaaacac aaacttcagg cgagaaaaaa ggtgtatata aacatcttat gaccggggtt | 720 |
| tcccatatgt taccgcttgt cgttgccggc ggtttattga ttgctatttc gtttatgttc | 780 |
| ggtattgagg cgtttaaaga cgaaaacatc gcaggcggct tgccgaaagc attaatggat | 840 |
| atcggcggcg gtgcggcgtt ccacttaatg attgccgtat ttgcaggtta tgttgcattc | 900 |
| tctattgcag accgtccggg gttagccgta ggtcttatcg gcggtatgct tgccacatcc | 960 |
| gccggtgccg gtatttgggg cggtattatc gcgggttttc ttgccggtta tgtagtgaaa | 1020 |
| ttcctgaatg atgccattca actgccagcc agtttaactt cgttaaaacc gatttaatt | 1080 |
| ctgcctttat taggttcggc gatcgtcggc ttggccatga tttatttatt aaatccaccg | 1140 |
| gttgctgcgg caatgaatgc gctaaccgaa tggttaaaag gtttgggctc ggcaaacgcg | 1200 |
| ctggtgttgg gtcgcattct tggcggtatg atgtgtatcg atatgggcgg tccggtaaac | 1260 |
| aaagccgctt atgtattcgg tacgggcatg attggttcac aggtttatac gccgatggct | 1320 |

-continued

```
gcggtaatgg ctgcgggtat ggtaccgcct ttaggaatgg cgattgccac ctggattgcg    1380
cgcgctaaat ttaacgcaag ccaacgtgat gcgggtaaag cttcattcgt actaggttta    1440
tgctttattt ccgaaggtgc gttaccgttt gttgccgccg accctgtacg cgtgattgtt    1500
tcaagtgtaa ttggcggagc cattgccggc gcaatttcta tgagccttgc cattacgctg    1560
caagcgcctc acggcggttt attcgtgatt ccgtttgtgt cgcaaccgtt aatgtatttg    1620
ggtgcgattg ccgtaggcgc cttaacaacc ggcgttcttt acgcaattat caaaccgaaa    1680
caagctgcgg aataa                                                     1695
```

<210> SEQ ID NO 4
<211> LENGTH: 564
<212> TYPE: PRT
<213> ORGANISM: Basfia succiniciproducens
<220> FEATURE:
<221> NAME/KEY: MISC_FEATURE
<222> LOCATION: (1)..(526)
<223> OTHER INFORMATION: amino acid sequence of the enzyme encoded by the above fruA-gene

<400> SEQUENCE: 4

```
Met Lys Asp Lys Pro Met Asn Ile Phe Leu Thr Gln Ser Pro Asn Leu
1               5                   10                  15

Gly Arg Ala Lys Ala Phe Leu Leu His Gln Val Leu Ala Ala Ala Val
            20                  25                  30

Lys Gln Gln Asn His Gln Leu Val Glu Asn Ala Glu Ala Asp Leu
        35                  40                  45

Ala Ile Val Phe Gly Lys Thr Leu Pro Asn Leu Thr Ala Leu Leu Gly
    50                  55                  60

Lys Lys Val Tyr Leu Ala Asp Glu Glu Gln Ala Leu Asn Ala Pro Glu
65                  70                  75                  80

Asn Thr Val Ala Gln Ala Leu Thr Glu Ala Val Asp Tyr Val Gln Pro
                85                  90                  95

Ala Gln Gln Asp Val Gln Pro Ala Thr Ala Ser Gly Met Lys Asn Ile
            100                 105                 110

Val Ala Val Thr Ala Cys Pro Thr Gly Val Ala His Thr Phe Met Ser
        115                 120                 125

Ala Glu Ala Ile Thr Thr Tyr Cys Gln Gln Gln Gly Trp Asn Val Lys
    130                 135                 140

Val Glu Thr Arg Gly Gln Val Gly Ala Asn Asn Ile Ile Ser Ala Glu
145                 150                 155                 160

Asp Val Ala Ala Ala Asp Leu Val Phe Ile Ala Thr Asp Ile Asn Val
                165                 170                 175

Asp Leu Ser Lys Phe Lys Gly Lys Pro Met Tyr Arg Thr Ser Thr Gly
            180                 185                 190

Leu Ala Leu Lys Lys Thr Ala Gln Glu Phe Asp Lys Ala Phe Lys Glu
        195                 200                 205

Ala Thr Ile Tyr Gln Gly Glu Glu Thr Thr Thr Thr Glu Thr Gln
    210                 215                 220

Thr Ser Gly Glu Lys Lys Gly Val Tyr Lys His Leu Met Thr Gly Val
225                 230                 235                 240

Ser His Met Leu Pro Leu Val Val Ala Gly Gly Leu Leu Ile Ala Ile
                245                 250                 255

Ser Phe Met Phe Gly Ile Glu Ala Phe Lys Asp Glu Asn Ile Ala Gly
            260                 265                 270

Gly Leu Pro Lys Ala Leu Met Asp Ile Gly Gly Gly Ala Ala Phe His
```

```
            275                 280                 285
Leu Met Ile Ala Val Phe Ala Gly Tyr Val Ala Phe Ser Ile Ala Asp
    290                 295                 300

Arg Pro Gly Leu Ala Val Gly Leu Ile Gly Gly Met Leu Ala Thr Ser
305                 310                 315                 320

Ala Gly Ala Gly Ile Leu Gly Gly Ile Ile Ala Gly Phe Leu Ala Gly
                325                 330                 335

Tyr Val Val Lys Phe Leu Asn Asp Ala Ile Gln Leu Pro Ala Ser Leu
            340                 345                 350

Thr Ser Leu Lys Pro Ile Leu Ile Leu Pro Leu Leu Gly Ser Ala Ile
        355                 360                 365

Val Gly Leu Ala Met Ile Tyr Leu Leu Asn Pro Val Ala Ala Ala
    370                 375                 380

Met Asn Ala Leu Thr Glu Trp Leu Lys Gly Leu Gly Ser Ala Asn Ala
385                 390                 395                 400

Leu Val Leu Gly Ala Ile Leu Gly Gly Met Met Cys Ile Asp Met Gly
                405                 410                 415

Gly Pro Val Asn Lys Ala Ala Tyr Val Phe Gly Thr Gly Met Ile Gly
            420                 425                 430

Ser Gln Val Tyr Thr Pro Met Ala Ala Val Met Ala Ala Gly Met Val
        435                 440                 445

Pro Pro Leu Gly Met Ala Ile Ala Thr Trp Ile Ala Arg Ala Lys Phe
    450                 455                 460

Asn Ala Ser Gln Arg Asp Ala Gly Lys Ala Ser Phe Val Leu Gly Leu
465                 470                 475                 480

Cys Phe Ile Ser Glu Gly Ala Leu Pro Phe Ala Ala Asp Pro Val
                485                 490                 495

Arg Val Ile Val Ser Ser Val Ile Gly Gly Ala Ile Ala Gly Ala Ile
            500                 505                 510

Ser Met Ser Leu Ala Ile Thr Leu Gln Ala Pro His Gly Gly Leu Phe
        515                 520                 525

Val Ile Pro Phe Val Ser Gln Pro Leu Met Tyr Leu Gly Ala Ile Ala
    530                 535                 540

Val Gly Ala Leu Thr Thr Gly Val Leu Tyr Ala Ile Ile Lys Pro Lys
545                 550                 555                 560

Gln Ala Ala Glu

<210> SEQ ID NO 5
<211> LENGTH: 4285
<212> TYPE: DNA
<213> ORGANISM: artificial sequence
<220> FEATURE:
<223> OTHER INFORMATION: complete nucleotide sequence of plasmid pSacB

<400> SEQUENCE: 5
tcgagaggcc tgacgtcggg cccggtacca cgcgtcatat gactagttcg gacctaggga      60
tatcgtcgac atcgatgctc ttctgcgtta attaacaatt gggatcctct agactccata     120
ggccgctttc ctggctttgc ttccagatgt atgctctcct ccggagagta ccgtgacttt     180
attttcggca caaatacagg ggtcgatgga taaatacggc gatagtttcc tgacggatga     240
tccgtatgta ccggcggaag acaagctgca aacctgtcag atggagattg atttaatggc     300
ggatgtgctg agagcaccgc cccgtgaatc gcagaactg atccgctatg tgtttgcgga     360
tgattggccg gaataaataa agccgggctt aatacagatt aagcccgtat agggtattat     420
```

```
tactgaatac caaacagctt acggaggacg gaatgttacc cattgagaca accagactgc    480
cttctgatta ttaatatttt tcactattaa tcagaaggaa taaccatgaa ttttacccgg    540
attgacctga atacctggaa tcgcagggaa cactttgccc tttatcgtca gcagattaaa    600
tgcggattca gcctgaccac caaactcgat attaccgctt tgcgtaccgc actggcggag    660
acaggttata agttttatcc gctgatgatt tacctgatct cccgggctgt taatcagttt    720
ccggagttcc ggatggcact gaaagacaat gaacttattt actgggacca gtcagacccg    780
gtctttactg tctttcataa agaaaccgaa acattctctg cactgtcctg ccgttatttt    840
ccggatctca gtgagtttat ggcaggttat aatgcggtaa cggcagaata tcagcatgat    900
accagattgt ttccgcaggg aaatttaccg gagaatcacc tgaatatatc atcattaccg    960
tgggtgagtt ttgacgggat taacctgaa catcaccgga aatgatgatt attttgcccc   1020 ggttttacg atggcaaagt ttcagcagga aggtgaccgc gtattattac ctgtttctgt    1080
acaggttcat catgcagtct gtgatggctt tcatgcagca cggtttatta atacacttca    1140
gctgatgtgt gataacatac tgaaataaat taattaattc tgtatttaag ccaccgtatc    1200
cggcaggaat ggtggctttt tttttatatt ttaaccgtaa tctgtaattt cgtttcagac    1260
tggttcagga tgagctcgct tggactcctg ttgatagatc cagtaatgac ctcagaactc    1320
catctggatt tgttcagaac gctcggttgc cgccgggcgt tttttattgg tgagaatcca    1380
agcactagcg cgcgccggc cggcccggtg tgaaataccg cacagatgcg taaggagaaa    1440
ataccgcatc aggcgctctt ccgcttcctc gctcactgac tcgctgcgct cggtcgttcg    1500
gctgcggcga gcggtatcag ctcactcaaa ggcggtaata cggttatcca gaatcagg     1560 ggataacgca ggaaagaaca tgtgagcaaa aggccagcaa aaggccagga accgtaaaaa    1620
ggccgcgttg ctggcgtttt tccataggct ccgcccccct gacgagcatc acaaaaatcg    1680
acgctcaagt cagaggtggc gaaacccgac aggactataa agataccagg cgtttccccc    1740
tggaagctcc ctcgtgcgct ctcctgttcc gaccctgccg cttaccggat acctgtccgc    1800
ctttctccct tcgggaagcg tggcgctttc tcatagctca cgctgtaggt atctcagttc    1860
ggtgtaggtc gttcgctcca agctgggctg tgtgcacgaa ccccccgttc agcccgaccg    1920
ctgcgcctta tccggtaact atcgtcttga gtccaacccg gtaagacacg acttatcgcc    1980
actggcagca gccactggta acaggattag cagagcgagg tatgtaggcg gtgctacaga    2040
gttcttgaag tggtggccta actacggcta cactagaagg acagtatttg gtatctgcgc    2100
tctgctgaag ccagttacct tcggaaaaag agttggtagc tcttgatccg gcaaacaaac    2160
caccgctggt agcggtggtt ttttgtttg caagcagcag attacgcgca gaaaaaaagg    2220
atctcaagaa gatcctttga tcttttctac ggggtctgac gctcagtgga acgaaaactc    2280
acgttaaggg attttggtca tgagattatc aaaaaggatc ttcacctaga tccttttaaa    2340
ggccggccgc ggccgccatc ggcattttct tttgcgtttt tatttgttaa ctgttaattg    2400
tccttgttca aggatgctgt ctttgacaac agatgttttt ttgcctttga tgttcagcag    2460
gaagctcggc gcaaacgttg attgtttgtc tgcgtagaat cctctgtttg tcatatagct    2520
tgtaatcacg acattgtttc ctttcgcttg aggtacagcg aagtgtgagt aagtaaaggt    2580
tacatcgtta ggatcaagat ccatttttaa cacaaggcca gttttgttca gcggcttgta    2640
tgggccagtt aaagaattag aaacataacc aagcatgtaa atatcgttag acgtaatgcc    2700
gtcaatcgtc attttgatc cgcgggagtc agtgaacagg taccatttgc cgttcatttt    2760
aaagacgttc gcgcgttcaa tttcatctgt tactgtgtta gatgcaatca gcggtttcat    2820
```

```
cacttttttc agtgtgtaat catcgtttag ctcaatcata ccgagagcgc cgtttgctaa    2880
ctcagccgtg cgttttttat cgctttgcag aagttttga ctttcttgac ggaagaatga    2940
tgtgcttttg ccatagtatg ctttgttaaa taaagattct tcgccttggt agccatcttc    3000
agttccagtg tttgcttcaa atactaagta tttgtggcct ttatcttcta cgtagtgagg    3060
atctctcagc gtatggttgt cgcctgagct gtagttgcct tcatcgatga actgctgtac    3120
attttgatac gttttccgt caccgtcaaa gattgattta taatcctcta caccgttgat    3180
gttcaaagag ctgtctgatg ctgatacgtt aacttgtgca gttgtcagtg tttgtttgcc    3240
gtaatgttta ccgagaaat cagtgtagaa taaacggatt tttccgtcag atgtaaatgt     3300
ggctgaacct gaccattctt gtgtttggtc ttttaggata gaatcatttg catcgaattt    3360
gtcgctgtct ttaaagacgc ggccagcgtt tttccagctg tcaatagaag tttcgccgac    3420 ttttgatag aacatgtaaa tcgatgtgtc atccgcattt ttaggatctc cggctaatgc     3480
aaagacgatg tggtagccgt gatagtttgc gacagtgccg tcagcgtttt gtaatggcca    3540
gctgtcccaa acgtccaggc cttttgcaga agagatattt ttaattgtgg acgaatcaaa    3600
ttcagaaact tgatatttt catttttttg ctgttcaggg atttgcagca tatcatggcg     3660
tgtaatatgg gaaatgccgt atgtttcctt atatggcttt tggttcgttt ctttcgcaaa    3720
cgcttgagtt gcgcctcctg ccagcagtgc ggtagtaaag gttaatactg ttgcttgttt    3780
tgcaaacttt ttgatgttca tcgttcatgt ctcctttttt atgtactgtg ttagcggtct    3840
gcttcttcca gccctcctgt ttgaagatgg caagttagtt acgcacaata aaaaaagacc    3900
taaaatatgt aaggggtgac gccaaagtat acactttgcc ctttacacat tttaggtctt    3960
gcctgcttta tcagtaacaa acccgcgcga tttactttc gacctcattc tattagactc     4020
tcgtttggat tgcaactggt ctattttcct cttttgtttg atagaaaatc ataaaggat    4080 ttgcagacta cgggcctaaa gaactaaaaa atctatctgt ttcttttcat tctctgtatt    4140
ttttatagtt tctgttgcat gggcataaag ttgcctttt aatcacaatt cagaaaatat     4200
cataatatct catttcacta aataatagtg aacggcaggt atatgtgatg ggttaaaaag    4260
gatcggcggc cgctcgattt aaatc                                          4285

<210> SEQ ID NO 6
<211> LENGTH: 7074
<212> TYPE: DNA
<213> ORGANISM: artificial sequence
<220> FEATURE:
<223> OTHER INFORMATION: complete nucleotide sequence of plasmid
      pSacB_delta_ldhA

<400> SEQUENCE: 6
tcgagaggcc tgacgtcggg cccggtacca cgcgtcatat gactagttcg gacctaggga      60
tgggtcagcc tgaacgaacc gcacttgtat gtaggtagtt ttgaccgccc gaatattcgt     120
tataccttgg tggaaaaatt caaaccgatg gagcaattat acaattttgt ggcggcgcaa     180
aaaggtaaaa gcggtatcgt ctattgcaac agccgtagca aagtggagcg cattgcggaa     240
gccctgaaga aaagaggcat ttccgcagcc gcttatcatg cgggcatgga gccgtcgcag     300
cgggaagcgg tgcaacaggc gtttcaacgg ataatattc aagtggtggt ggcgaccatt      360
gcttttggta tggggatcaa caaatctaat gtgcgttttg tggcgcattt tgatttatct     420
cgcagcattg aggcgtatta tcaggaaacc gggcgcgcgg ggcgggacga cctgccggcg     480
gaagcggtac tgttttacga gccggcggat tatgcctggt tgcataaaat tttattggaa     540
```

```
gagccggaaa gcccgcaacg ggatattaaa cggcataagc tggaagccat cggcgaattt        600
gccgaaagcc agacctgccg tcgtttagtg ctgttaaatt atttcggcga aaaccgccaa        660
acgccatgta ataactgtga tatctgcctc gatccgccga aaaaatatga cggattatta        720
gacgcgcaga aaatcctttc gaccatttat cgcaccgggc aacgtttcgg cacgcaatac        780
gtaatcggcg taatgcgcgg tttgcagaat cagaaaataa agaaaatca acatgatgag         840
ttgaaagtct acggaattgg caaagataaa agcaaagaat actggcaatc ggtaattcgt        900
cagctgattc atttgggctt tgtgcaacaa atcatcagcg atttcggcat ggggaccaga        960
ttacagctca ccgaaagcgc gcgtcccgtg ctgcgcggcg aagtgtcttt ggaactggcc       1020
atgccgagat tatcttccat taccatggta caggctccgc aacgcaatgc ggtaaccaac       1080
tacgacaaag atttatttgc ccgcctgcgt ttcctgcgca aacagattgc cgacaaagaa       1140
aacattccgc cttatattgt gttcagtgac gcgaccttgc aggaaatgtc gttgtatcag       1200
ccgaccagca aagtggaaat gctgcaaatc aacggtgtcg cgccatcaa atggcagcgc        1260
ttcggacagc ctttatggc gattattaaa gaacatcagg ctttgcgtaa agcgggtaag        1320
aatccgttgg aattgcaatc ttaaaatttt taacttttg accgcactt taaggttagc         1380
aaattccaat aaaaagtgcg gtgggttttc gggaattttt aacgcgctga tttcctcgtc       1440
ttttcaattt yttcgyctcc atttgttcgg yggttgccgg atcctttctt gactgagatc       1500
cataagagag tagaatagcg ccgcttatat ttttaatagc gtacctaatc gggtacgctt       1560
tttttatgcg gaaaatccat attttttctac cgcactttt cttttaaagat ttatacttaa     1620
gtctgtttga ttcaatttat ttggaggttt tatgcaacac attcaactgg ctcccgattt       1680
aacattcagt cgcttaattc aaggattctg gcggttaaaa agctggcgga atcgccgca        1740
ggaattgctt acattcgtta agcaaggatt agaattaggc gttgatacgc tggatcatgc       1800
cgcttgttac ggggctttta cttccgaggc ggaattcgga cgggcgctgg cgctggataa       1860
atccttgcgc gcacagctta ctttggtgac caaatgcggg attttgtatc ctaatgaaga       1920
attacccgat ataaaatccc atcactatga caacagctac cgccatatta tgtggtcggc       1980
gcaacgttcc attgaaaaac tgcaatgcga ctatttagat gtattgctga ttcaccgwct      2040
ttctcctgt gcggatcccg aacaaatcgc gcgggctttt gatgaacttt atcaaaccgg        2100
raaagtacgt tatttcgggg tatctaacta tacgccggct aagttcgcca tgttgcaatc      2160
ttatgtgaat cagccgttaa tcactaatca aattgagatt cgcctcttc atcgtcaggc      2220
ttttgatgac ggtaccctgg atttttact ggaaaaacgt attcaaccga tggcatggtc       2280
gccacttgcc ggcggtcgtt tattcaatca ggatgagaac agtcgggcgg tgcaaaaaac      2340
attactcgaa atcggtgaaa cgaaggaga acccgttta gatacattgg cttatgcctg       2400
gttattggcg catccggcaa aaattatgcc ggttatgggg tccggtaaaa ttgaacgggt      2460
aaaaagcgcg gcggatgcgt tacgaatttc cttcactgag gaagaatgga ttaaggttta    2520
tgttgccgca cagggacggg atattccgta acatcatccg tctaatcctg cgtatctggg     2580
gaaagatgcg tcatcgtaag aggtctataa tattcgtcgt tttgataagg gtgccatatc     2640
cggcacccgt taaaatcaca ttgcgttcgc aacaaaatta ttccttacga atagcattca     2700
cctctttta cagatgttga atatccgtat cggcaaaaat atcctctata tttgcggtta     2760
aacggcgccg ccagttagca tattgagtgc tggttcccgg aatattgacg ggttcggtca     2820
taccgagcca gtcttcaggt tggaatcccc atcgtcgaca tcgatgctct tctgcgttaa    2880
```

```
ttaacaattg ggatcctcta gactccatag gccgctttcc tggctttgct tccagatgta    2940
tgctctcctc cggagagtac cgtgacttta ttttcggcac aaatacaggg gtcgatggat    3000
aaatacggcg atagtttcct gacggatgat ccgtatgtac cggcggaaga caagctgcaa    3060
acctgtcaga tggagattga tttaatggcg gatgtgctga gagcaccgcc ccgtgaatcc    3120
gcagaactga tccgctatgt gttttgcggat gattggccgg aataaataaa gccgggctta    3180
atacagatta agcccgtata gggtattatt actgaatacc aaacagctta cggaggacgg    3240
aatgttaccc attgagacaa ccagactgcc ttctgattat taatattttt cactattaat    3300
cagaaggaat aaccatgaat tttacccgga ttgacctgaa tacctggaat cgcagggaac    3360
actttgccct ttatcgtcag cagattaaat gcggattcag cctgaccacc aaactcgata    3420
ttaccgcttt gcgtaccgca ctggcggaga caggttataa gttttatccg ctgatgattt    3480
acctgatctc ccgggctgtt aatcagtttc cggagttccg gatggcactg aaagacaatg    3540
aacttattta ctgggaccag tcagacccgg tctttactgt ctttcataaa gaaaccgaaa    3600
cattctctgc actgtcctgc cgttattttc cggatctcag tgagtttatg gcaggttata    3660
atgcggtaac ggcagaatat cagcatgata ccagattgtt ccgcagggaa aatttaccgg    3720
agaatcacct gaatatatca tcattaccgt gggtgagttt tgacgggatt taacctgaac    3780
atcaccggaa atgatgatta ttttgccccg gtttttacga tggcaaagtt tcagcaggaa    3840
ggtgaccgcg tattattacc tgtttctgta caggttcatc atgcagtctg tgatggcttt    3900
catgcagcac ggtttattaa tacacttcag ctgatgtgtg ataacatact gaaataaatt    3960
aattaattct gtatttaagc caccgtatcc ggcaggaatg gtggcttttt ttttatattt    4020
taaccgtaat ctgtaatttc gtttcagact ggttcaggat gagctcgctt ggactcctgt    4080
tgatagatcc agtaatgacc tcagaactcc atctggattt gttcagaacg ctcggttgcc    4140
gccgggcgtt ttttattggt gagaatccaa gcactagcgg cgcgccggcc ggcccggtgt    4200
gaaataccgc acagatgcgt aaggagaaaa taccgcatca ggcgctcttc cgcttcctcg    4260
ctcactgact cgctgcgctc ggtcgttcgg ctgcggcgag cggtatcagc tcactcaaag    4320
gcggtaatac ggttatccac agaatcaggg gataacgcag gaaagaacat gtgagcaaaa    4380
ggccagcaaa aggccaggaa ccgtaaaaag gccgcgttgc tggcgttttt ccataggctc    4440
cgcccccctg acgagcatca caaaaatcga cgctcaagtc agaggtggcg aaacccgaca    4500
ggactataaa gataccaggc gtttccccct ggaagctccc tcgtgcgctc tcctgttccg    4560
accctgccgc ttaccggata cctgtccgcc tttctccctt cgggaagcgt ggcgctttct    4620
catagctcac gctgtaggta tctcagttcg gtgtaggtcg ttcgctccaa gctgggctgt    4680
gtgcacgaac cccccgttca gcccgaccgc tgcgccttat ccggtaacta tcgtcttgag    4740
tccaacccgg taagacacga cttatcgcca ctggcagcag ccactggtaa caggattagc    4800
agagcgaggt atgtaggcgg tgctacagag ttcttgaagt ggtggcctaa ctacggctac    4860
actagaagga cagtatttgg tatctgcgct ctgctgaagc cagttacctt cggaaaaaga    4920
gttggtagct cttgatccgg caaacaaacc accgctggta gcggtggttt ttttgtttgc    4980
aagcagcaga ttacgcgcag aaaaaaagga tctcaagaag atcctttgat cttttctacg    5040
gggtctgacg ctcagtggaa cgaaaactca cgttaaggga ttttggtcat gagattatca    5100
aaaaggatct tcacctagat ccttttaaag gccggccgcg gccgccatcg gcattttctt    5160
ttgcgttttt atttgttaac tgttaattgt ccttgttcaa ggatgctgtc tttgacaaca    5220
gatgttttct tgcctttgat gttcagcagg aagctcggcg caaacgttga ttgtttgtct    5280
```

```
gcgtagaatc ctctgtttgt catatagctt gtaatcacga cattgtttcc tttcgcttga   5340
ggtacagcga agtgtgagta agtaaaggtt acatcgttag gatcaagatc cattttaac    5400 acaaggccag ttttgttcag cggcttgtat gggccagtta agaattaga aacataacca    5460 agcatgtaaa tatcgttaga cgtaatgccg tcaatcgtca ttttgatcc gcgggagtca    5520 gtgaacaggt accatttgcc gttcatttta aagacgttcg cgcgttcaat ttcatctgtt   5580
actgtgttag atgcaatcag cggtttcatc actttttca gtgtgtaatc atcgtttagc    5640
tcaatcatac cgagagcgcc gtttgctaac tcagccgtgc gttttttatc gctttgcaga   5700 agttttgac tttcttgacg gaagaatgat gtgcttttgc catagtatgc tttgttaaat    5760
aaagattctt cgccttggta gccatcttca gttccagtgt ttgcttcaaa tactaagtat   5820
ttgtggcctt tatcttctac gtagtgagga tctctcagcg tatggttgtc gcctgagctg   5880
tagttgcctt catcgatgaa ctgctgtaca ttttgatacg ttttccgtc accgtcaaag    5940 attgatttat aatcctctac accgttgatg ttcaaagagc tgtctgatgc tgatacgtta   6000
acttgtgcag ttgtcagtgt ttgtttgccg taatgtttac cggagaaatc agtgtagaat   6060
aaacggattt ttccgtcaga tgtaaatgtg gctgaacctg accattcttg tgtttggtct   6120
tttaggatag aatcatttgc atcgaatttg tcgctgtctt taaagacgcg gccagcgttt   6180
ttccagctgt caatagaagt ttcgccgact ttttgataga acatgtaaat cgatgtgtca   6240
tccgcatttt taggatctcc ggctaatgca aagacgatgt ggtagccgtg atagtttgcg   6300
acagtgccgt cagcgttttg taatggccag ctgtcccaaa cgtccaggcc ttttgcagaa   6360
gagatatttt taattgtgga cgaatcaaat tcagaaactt gatatttttc attttttgc    6420 tgttcaggga tttgcagcat atcatggcgt gtaatatggg aaatgccgta tgtttccta   6480 tatggctttt ggttcgtttc tttcgcaaac gcttgagttg cgcctcctgc cagcagtgcg   6540
gtagtaaagg ttaatactgt tgcttgtttt gcaaactttt tgatgttcat cgttcatgtc   6600 tccttttta tgtactgtgt tagcggtctg cttcttccag ccctcctgtt tgaagatggc    6660
aagttagtta cgcacaataa aaaaagacct aaaatatgta aggggtgacg ccaaagtata   6720
cactttgccc tttacacatt ttaggtcttg cctgctttat cagtaacaaa cccgcgcgat   6780
ttacttttcg acctcattct attagactct cgtttggatt gcaactggtc tattttcctc   6840
ttttgtttga tagaaaatca taaaggatt tgcagactac gggcctaaag aactaaaaaa    6900
tctatctgtt tcttttcatt ctctgtattt tttatagttt ctgttgcatg gcataaagt    6960 tgccttttta atcacaattc agaaaatatc ataatatctc atttcactaa ataatagtga   7020
acggcaggta tatgtgatgg gttaaaaagg atcggcggcc gctcgattta aatc          7074
```

<210> SEQ ID NO 7
<211> LENGTH: 7183
<212> TYPE: DNA
<213> ORGANISM: artificial sequence
<220> FEATURE:
<223> OTHER INFORMATION: complete nucleotide sequence of plasmid
     pSacB_delta_pflA

<400> SEQUENCE: 7

```
tcgagtcaat gcggatttga cttatgatgt ggcaaacaac cgatttccga ttattactac     60
acgtaaaagt tattggaaag cggcgattgc ggagtttctg ggttatatcc gcggctacga   120
taatgcggcg gatttccgta aattaggagc aaaaacctgg gatgccaacg ctaatgaaaa   180
tcaggtatgg ctgaataacc ctcatcgcaa aggcaccgac gacatggggc gcgtttacgg   240
```

```
cgtacagggc agagcctggc gtaagcctaa cggcgaaacc gttgatcaat tacgcaaaat    300
tgtcaacaat ttaagtcgcg gcattgatga tcgcggcgaa attctgacct ttttaaaccc    360
gggcgaattc gatctcggtt gtctgcgccc ttgtatgtac aatcacacgt tttctttgct    420
gggcgatacg ctttatttaa ccagttatca acgctcctgt gacgtacctt taggcttgaa    480
tttcaatcaa attcaagtat ttacattctt agctttaatg gcgcagatta ccggtaaaaa    540
agccggtcag gcatatcaca aaatcgtcaa tgcgcatatt tacgaagacc agctggaact    600
aatgcgcgac gtgcagttaa aacgcgaacc gttcccgtcg ccaaaactgg aaattaatcc    660
ggacattaaa acccttgaag atttagaaac ctgggtaacc atggatgatt caacgtcgt    720 tggttaccaa tgccacgaac cgataaaata tccgttctcg gtataaaccg acaaaagtgc    780
ggtcaaaaat ttaatatttt catctgttat agaaaatatt tttcaacata aatctaggg    840 atgcctgttt ggcgtccgta aatacgcaga aaatattaa attttttgacc gcactttttt    900 catctcaatt aacagcctga taattcttat ggatcaacaa attagctttg acgaaaaaat    960
gatgaatcga gctcttttcc ttgccgacaa ggcggaagct ttaggggaaa ttcccgtagg    1020
tgccgtattg gtggatgaac ggggcaatat cattggtgaa ggctggaacc tctctattgt    1080
gaactcggat cccaccgccc atgccgaaat tattgcgttg cgtaacgccg cgcagaaaat    1140
ccaaaattac cgcctgctca ataccacttt atacgtgact ttagaaccct gcaccatgtg    1200
cgccggcgcg attttacaca gccgaatcaa acgcttggta ttcggggcgt ccgattacaa    1260
aaccggtgcg gtgggttcca gatttcattt ttttgaggat tataaaatga atcatggggt    1320
tgagatcaca agcggtgtct tacaggatca atgcagtcag aagttaagcc gcttttttcca    1380 aaagcgcagg gaacagaaaa aacaacaaaa agctaccgca cttttacaac accccggct    1440 taactcctct gaaaaatagt gacaaaaaaa ccgtcataat gtttacgacg gttttttttat   1500 ttcttaatat gcccttaaat aatcaacaaa atatagcaag aagattatag caaagaattt    1560
cgtttttttc agagaatagt caaatcttcg caaaaaacta ccgcactttt atccgcttta    1620
atcaggggaa ttaaaacaaa aaaattccgc ctattgaggc ggaatttatt aagcaataag    1680
acaaactctc aattacattg attgtgtaaa cgtacgagtg atgacgtctt gttgttgctc    1740
tttagttaat gagttgaaac gaaccgcgta acctgaaaca cgaatggtta attgcgggta    1800 ttttccgga ttttccatcg cgtctaacaa catttcacgg ttaagaacgt taacattcaa    1860
gtgttgaccg ccttccactg tcgcttcatg atggaaataa ccgtccatta aaccggcaag    1920
gttgcgtttt tgcgcttcgt catctttacc taatgcgttc ggtacgatag agaaggtata    1980
tgaaataccg tctttcgcgt aagcgaacgg aagtttagcc acagaagtaa gtgaagcaac    2040
cgcacctttt tggtcacgac cgtgcattgg gtttgcaccc ggtccgaatg gcgcgcctgc    2100
tcgacgaccg tccggagtat taccggtttt cttaccgtat accacgttag aagtgatagt    2160
caggatagat tgtgtcggag ttgcgttgcg gtaagttttg tgttttgaa cttttttcat    2220 gaaacgttca actaagtcta ccgctaaatc atcaacacgc ggatcattgt taccgaattg    2280
cggatattcg ccttcaattt cgaagtcgat agcaacattc gaggccacga cattaccgtc    2340
tttatctttg atgtcgccgc gaatcggttt aactttcgca tatttgattg cggataatga    2400
gtccgcagcc acggaaagac ccgcgatacc gcaagccatt gtacggaata cgtcgcgatc    2460
gtggaacgcc atcaatgccg cttcatatgc atatttatcg tgcatgaagt ggatgatgtt    2520
caatgcggtt acatattgag tcgccaacca gtccatgaaa ctgtccatac gttcgattac    2580
```

```
ggtatcgaaa ttcaatactt cgtctgtaat cggcgcagtt ttaggaccga cttgcatacc    2640 attttttctca tcgataccgc cgttaattgc gtataacata gttttagcta agtttgcgcg    2700
cgcaccgaag aattgcattt gtttacctac gaccatcggt gatacgcagc atgcgattgc    2760
atagtcatcg ttgttgaagt caggacgcat taagtcatca ttttcgtatt gtacggagga    2820
agtatcaata gatactttcg cacagaaacg tttgaacgct tcaggtaatt gttcggacca    2880
aagaatagtt aagtttggtt ccggagaagt acccatagtg tataaagtat gtaatacgcg    2940
gaagctgttt ttagttacca acggacgacc gtctaagccc ataccggcga tagtttcggt    3000
tgccctctag actccatagg ccgctttcct ggctttgctt ccagatgtat gctctcctcc    3060
ggagagtacc gtgactttat tttcggcaca aatacagggg tcgatggata aatacggcga    3120
tagtttcctg acggatgatc cgtatgtacc ggcggaagac aagctgcaaa cctgtcagat    3180
ggagattgat ttaatggcgg atgtgctgag agcaccgccc cgtgaatccg cagaactgat    3240
ccgctatgtg tttgcggatg attggccgga ataaataaag ccgggcttaa tacagattaa    3300
gcccgtatag ggtattatta ctgaatacca aacagcttac ggaggacgga atgttaccca    3360
ttgagacaac cagactgcct tctgattatt aatattttc actattaatc agaaggaata    3420
accatgaatt ttacccggat tgacctgaat acctggaatc gcagggaaca ctttgcccctt    3480 tatcgtcagc agattaaatg cggattcagc ctgaccacca aactcgatat taccgctttg    3540
cgtaccgcac tggcggagac aggttataag ttttatccgc tgatgattta cctgatctcc    3600
cgggctgtta atcagttcc ggagttccgg atggcactga agacaatga acttatttac    3660 tgggaccagt cagacccggt ctttactgtc tttcataaag aaaccgaaac attctctgca    3720
ctgtcctgcc gttattttcc ggatctcagt gagtttatgg caggttataa tgcggtaacg    3780
gcagaatatc agcatgatac cagattgttt ccgcagggaa atttaccgga gaatcacctg    3840
aatatatcat cattaccgtg ggtgagtttt gacgggattt aacctgaaca tcaccggaaa    3900
tgatgattat ttttgccccgg ttttacgat ggcaaagttt cagcaggaag gtgaccgcgt    3960
attattacct gtttctgtac aggttcatca tgcagtctgt gatggctttc atgcagcacg    4020
gtttattaat acacttcagc tgatgtgtga taacatactg aaataaatta attaattctg    4080
tatttaagcc accgtatccg gcaggaatgg tggctttttt tttataatttt aaccgtaatc    4140 tgtaatttcg tttcagactg gttcaggatg agctcgcttg gactcctgtt gatagatcca    4200
gtaatgacct cagaactcca tctggatttg ttcagaacgc tcggttgccg ccgggcgttt    4260
tttattggtg agaatccaag cactagcggc gcgccggccg gccccggtgtg aaataccgca    4320 cagatgcgta aggagaaat accgcatcag gcgctcttcc gcttcctcgc tcactgactc    4380
gctgcgctcg tcgttcggc tgcggcgagc ggtatcagct cactcaaagg cggtaatacg    4440
gttatccaca gaatcagggg ataacgcagg aaagaacatg tgagcaaaag gccagcaaaa    4500
ggccaggaac cgtaaaaagg ccgcgttgct ggcgtttttc cataggctcc gccccctga    4560 cgagcatcac aaaaatcgac gctcaagtca gaggtggcga aacccgacag gactataaag    4620
ataccaggcg tttccccctg gaagctccct cgtgcgctct cctgttccga ccctgccgct    4680
taccggatac ctgtccgcct ttctcccttc gggaagcgtg cgctttctc atagctcacg    4740 ctgtaggtat ctcagttcgg tgtaggtcgt tcgctccaag ctgggctgtg tgcacgaacc    4800
ccccgttcag cccgaccgct gcgccttatc cggtaactat cgtcttgagt ccaacccggt    4860
aagacacgac ttatcgccac tggcagcagc cactggtaac aggattagca gagcgaggta    4920
tgtaggcggt gctacagagt tcttgaagtg gtggcctaac tacggctaca ctagaaggac    4980
```

```
agtatttggt atctgcgctc tgctgaagcc agttaccttc ggaaaaagag ttggtagctc      5040
ttgatccggc aaacaaacca ccgctggtag cggtggtttt tttgtttgca agcagcagat      5100
tacgcgcaga aaaaaggat ctcaagaaga tcctttgatc ttttctacgg ggtctgacgc       5160
tcagtggaac gaaaactcac gttaagggat tttggtcatg agattatcaa aaaggatctt      5220
cacctagatc cttttaaagg ccggccgcgg ccgccatcgg catttctctt tgcgttttta      5280
tttgttaact gttaattgtc cttgttcaag gatgctgtct ttgacaacag atgttttctt      5340
gcctttgatg ttcagcagga agctcggcgc aaacgttgat tgtttgtctg cgtagaatcc      5400
tctgtttgtc atatagcttg taatcacgac attgtttcct ttcgcttgag gtacagcgaa      5460
gtgtgagtaa gtaaaggtta catcgttagg atcaagatcc atttttaaca caaggccagt      5520
tttgttcagc ggcttgtatg ggccagttaa agaattagaa acataaccaa gcatgtaaat      5580
atcgttagac gtaatgccgt caatcgtcat ttttgatccg cgggagtcag tgaacaggta      5640
ccatttgccg ttcattttaa agacgttcgc gcgttcaatt tcatctgtta ctgtgttaga      5700
tgcaatcagc ggtttcatca ctttttttcag tgtgtaatca tcgtttagct caatcatacc      5760
gagagcgccg tttgctaact cagccgtgcg ttttttatcg ctttgcagaa gttttttgact     5820 ttcttgacgg aagaatgatg tgcttttgcc atagtatgct ttgttaaata aagattcttc      5880
gccttggtag ccatcttcag ttccagtgtt tgcttcaaat actaagtatt tgtggccttt      5940
atcttctacg tagtgaggat ctctcagcgt atggttgtcg cctgagctgt agttgccttc      6000
atcgatgaac tgctgtacat tttgatacgt ttttccgtca ccgtcaaaga ttgatttata      6060
atcctctaca ccgttgatgt tcaaagagct gtctgatgct gatacgttaa cttgtgcagt      6120
tgtcagtgtt tgtttgccgt aatgtttacc ggagaaatca gtgtagaata aacggatttt      6180
tccgtcagat gtaaatgtgg ctgaacctga ccattcttgt gtttggtctt ttaggataga      6240
atcatttgca tcgaatttgt cgctgtcttt aaagacgcgg ccagcgtttt tccagctgtc      6300
aatagaagtt tcgccgactt tttgatagaa catgtaaatc gatgtgtcat ccgcattttt      6360
aggatctccg gctaatgcaa agacgatgtg gtagccgtga tagtttgcga cagtgccgtc      6420
agcgttttgt aatggccagc tgtcccaaac gtccaggcct tttgcagaag agatattttt      6480
aattgtggac gaatcaaatt cagaaacttg atatttttca ttttttttgct gttcagggat      6540 ttgcagcata tcatggcgtg taatatggga aatgccgtat gtttccttat atggcttttg      6600
gttcgtttct ttcgcaaacg cttgagttgc gcctcctgcc agcagtgcgg tagtaaaggt      6660
taatactgtt gcttgttttg caacttttt gatgttcatc gttcatgtct cctttttat       6720 gtactgtgtt agcggtctgc ttcttccagc cctcctgttt gaagatggca agttagttac      6780
gcacaataaa aaaagaccta aaatatgtaa ggggtgacgc caaagtatac actttgccct      6840
ttacacattt taggtcttgc ctgctttatc agtaacaaac ccgcgcgatt tactttcga      6900 cctcattcta ttagactctc gtttggattg caactggtct attttcctct tttgtttgat      6960
agaaaatcat aaaaggattt gcagactacg ggcctaaaga actaaaaaat ctatctgttt      7020
cttttcattc tctgtatttt ttatagtttc tgttgcatgg gcataaagtt gccttttaa      7080 tcacaattca gaaaatatca taatatctca tttcactaaa taatagtgaa cggcaggtat      7140
atgtgatggg ttaaaaagga tcggcggccg ctcgatttaa atc                        7183
```

<210> SEQ ID NO 8
<211> LENGTH: 7183
<212> TYPE: DNA

<213> ORGANISM: artificial sequence
<220> FEATURE:
<223> OTHER INFORMATION: complete nucleotide sequence of plasmid pSacB_fruA

<400> SEQUENCE: 8

| | | | | | |
|---|---|---|---|---|---|
| tcgagtagga | gtaactcaag | gtcaccgttt | gcgttttgtt | gccgaaggtg | cgcaggcaca | 60 |
| gcaggcgatt | gaagccatcg | ctaaagaaat | tgcggcgggc | ttgggtgagc | ctgtttccgc | 120 |
| cgttccgccg | gcagaaccgg | atactattga | agtcgctaac | ccggcgacac | cggaagttga | 180 |
| gcaaccaaaa | tccgacagta | tcgaagcggt | ttttgtgatt | aataatgaaa | acggtctgca | 240 |
| tgctcgtcct | gcggcgactt | tagtgaatga | agtcaaaaaa | tataatgcgt | cggtggcggt | 300 |
| tcgtaattta | gatcgcgacg | gtgggttagt | gagcgctaaa | agcatgatga | aaatcgttgc | 360 |
| attaggtgcg | acaaaaggtt | ctcgtctgca | ttttgtcgcc | accggtgaag | aagctcaaca | 420 |
| agcgattgac | ggtatcggtg | cggcaatcgc | ggcaggttta | ggagaataaa | caatggcaaa | 480 |
| agtggcaaca | attacattaa | acgccgccta | tgatttggtc | gggcgtttaa | aacgcattga | 540 |
| attgggcgaa | gtgaatacgg | tggaacccct | cggtttattc | cctgccggta | aaggtatcaa | 600 |
| tgtggctaag | gtgttgaatg | acttagatgt | tgaagtcgcg | gtcggtggtt | ttctcggtga | 660 |
| agataacgta | ggcgatttcg | agcatttatt | ccaacaacaa | ggtttgcagg | ataaattcca | 720 |
| gcgggttgcc | ggtaaaaccc | gaataaacgt | aaaaatcacc | gaaacggacg | cggatgtaac | 780 |
| ggatttgaat | tttcttggtt | atcaaatcag | tgaacaggat | tggcggaaat | ttaccgcaga | 840 |
| ttctctcgct | tattgtaaag | aattcgacat | cgttgccgtg | tgtggcagtt | tgccccgcgg | 900 |
| cgtaacggcg | gatatgtttc | aaagctggtt | aagtcaatta | catcaagcgg | gtgtaaaagt | 960 |
| cgtactagat | agtagtaatg | ccgcattaac | agcaggtctt | aaagcaaatc | cttggttagt | 1020 |
| gaaaccgaat | caccgcgaat | tagaagcctg | ggtcggccat | gagttaccga | ctttgaaaga | 1080 |
| catcattgac | gccgcaaaac | aattaaaagc | acaagggata | gccaatgtta | ttatttccat | 1140 |
| gggcgcaaac | ggctcattat | ggctaagtga | taacggcgtg | attttggctc | agccgccgaa | 1200 |
| atgtgaaaac | gtagtaagca | cagtcggtgc | cggcgattcg | atggtcgcag | gtttaattta | 1260 |
| tggttttgta | aataatttat | ctcaacaaga | aacattggcg | tttgcaagtg | cggtatctgc | 1320 |
| cttcgccgtt | tcacaaagta | acgtaggtgt | cagtgatcgc | aagttgctcg | acccaatctt | 1380 |
| agcaaatgta | aaaatcacaa | cgattgaagg | ataagccgat | gaatattttt | cttacgcaat | 1440 |
| caccaaattt | aggtcgtgca | aaagcgtttt | tattgcacca | ggttttggct | gccgcagtaa | 1500 |
| aacaatttcc | taatcaagca | taaagccttt | gtttatctca | aaacaaaggc | ttttttttata | 1560 |
| agtattccgc | tttgcccgaa | ctaatagaaa | aattggcaga | caaaagaagt | gttcatagca | 1620 |
| caggaggaac | aatatggatt | tcaatgcaat | tttaaatcaa | gttttaagtg | ccgctcagga | 1680 |
| aaccgttaag | aaaacggcaa | gcggcaatag | cacaacggat | aaagtggcaa | aaatcggtgg | 1740 |
| cggtgcagcg | gctatcggcg | tgctttcgat | gattttcggg | cgcaccggcg | gagcggggct | 1800 |
| tgcaaaatta | ggctcgcttg | ccgcattagg | cagccttgct | tatcaggctt | accaggatta | 1860 |
| tcaacataaa | caaagccaag | ttgtaccggt | tactgaaacg | gaatttaccc | aaagcgtaca | 1920 |
| acaatcggcg | gaactcagca | aagtgatttt | gcagcaatg | attgcggcgg | cggctgcaga | 1980 |
| cggcgcgatt | tccgaccagg | aacaacaagc | gattttaagc | caagccggcg | atgatgcgga | 2040 |
| agtacagcag | tggattcggc | aagaaatgta | tcaaccggca | acagtgcggg | aaatcgccca | 2100 |
| acaagtgggt | gataatcagg | cattagcatc | acaggtgtat | ctggcggcaa | gaatggtttg | 2160 |

```
cgccgattta gcacgcaaag aaattgtttt cttagcaaat ttagcgcaag cgttggggtt    2220
agatgaagcg cttgtagaac agttagaaaa acaggcgggt ttctgattta atcattccgc    2280
gatgtgcaaa gtgcggtcaa aaataacgat ttttttaccg cacttttgca tttgcaagac    2340
gtttcgaaaa tgcctgttct aacttctatt aaaacccttc ttctaaaatt ttctccaata    2400
actcaaatac cagcaacact cgtttgggag taatggtttg ataaggacgg tagaggtaaa    2460
ttccccaaat caaggtttcc tcattagaga agactacttg taactcgccg gaatcaagat    2520
aggatttaca gtcatgatac attatcggcg cgaaaatcct gccggataag accgccggta    2580
acaagctttt aatatcgctg gtgataaccg tcggcttagt tagaattatg ggttgttcac    2640
ccatcatcca gtcccatact ttgccggtct taggatttaa aatatagcct accggaaaat    2700
tggcggctaa atcaaaaacg tcttttggca atccggtttt agcgataaga ctaggtgctg    2760
ccacgatagg ctcttgtagg tcagtaatct ttttcgccac ccaatgatct tcgggcgtgc    2820
ggctgatgcg aataccgata tcaatttggt catccaccgc tttgagcgta tcgaaatccg    2880
tgcgccagtc aatctgaata tccggatagg gcgcaagtgc ggttagtaat cgcaataaaa    2940
ttttatccgc ataatcggaa ggcggtaacg taatccgcac taagccggaa aggctctctt    3000
ccgcatctag actccatagg ccgctttcct ggctttgctt ccagatgtat gctctcctcc    3060
ggagagtacc gtgactttat tttcggcaca aatacagggg tcgatggata aatacggcga    3120
tagtttcctg acgatgatc cgtatgtacc ggcggaagac aagctgcaaa cctgtcagat     3180
ggagattgat ttaatggcgg atgtgctgag agcaccgccc cgtgaatccg cagaactgat    3240
ccgctatgtg tttgccggatg attggccgga ataaataaag ccgggcttaa tacagattaa    3300
gcccgtatag ggtattatta ctgaatacca aacagcttac ggaggacgga atgttaccca    3360
ttgagacaac cagactgcct tctgattatt aatattttc actattaatc agaaggaata     3420
accatgaatt ttacccggat tgacctgaat acctggaatc gcagggaaca ctttgccctt    3480
tatcgtcagc agattaaatg cggattcagc ctgaccacca aactcgatat taccgctttg    3540
cgtaccgcac tggcggagac aggttataag ttttatccgc tgatgattta cctgatctcc    3600
cgggctgtta atcagtttcc ggagttccgg atggcactga agacaatga acttatttac     3660 tgggaccagt cagacccggt ctttactgtc tttcataaag aaaccgaaac attctctgca    3720
ctgtcctgcc gttattttcc ggatctcagt gagtttatgg caggttataa tgcggtaacg    3780
gcagaatatc agcatgatac cagattgttt ccgcagggaa atttaccgga gaatcacctg    3840
aatatatcat cattaccgtg ggtgagtttt gacgggattt aacctgaaca tcaccggaaa    3900
tgatgattat tttgccccgg ttttacgat ggcaaagttt cagcaggaag gtgaccgcgt     3960
attattacct gttctgtac aggttcatca tgcagtctgt gatggctttc atgcagcacg     4020
gtttattaat acacttcagc tgatgtgtga taacatactg aaataaatta attaattctg    4080
tatttaagcc accgtatccg gcaggaatgg tggcttttt tttatatttt aaccgtaatc     4140
tgtaatttcg tttcagactg gttcaggatg agctcgcttg gactcctgtt gatagatcca    4200
gtaatgacct cagaactcca tctggatttg ttcagaacgc tcggttgccg ccgggcgttt    4260
tttattggtg agaatccaag cactagcggc gcgccggccg gccggtgtg aaataccgca     4320 cagatgcgta aggagaaaat accgcatcag gcgctcttcc gcttcctcgc tcactgactc    4380
gctgcgctcg tcgttcggc tgcggcgagc ggtatcagct cactcaaagg cggtaatacg     4440
gttatccaca gaatcagggg ataacgcagg aaagaacatg tgagcaaaag gccagcaaaa    4500
ggccaggaac cgtaaaaagg ccgcgttgct ggcgtttttc cataggctcc gcccccctga    4560
```

```
cgagcatcac aaaaatcgac gctcaagtca gaggtggcga aacccgacag gactataaag    4620
ataccaggcg tttccccctg gaagctccct cgtgcgctct cctgttccga ccctgccgct    4680
taccggatac ctgtccgcct ttctcccttc gggaagcgtg gcgctttctc atagctcacg    4740
ctgtaggtat ctcagttcgg tgtaggtcgt tcgctccaag ctgggctgtg tgcacgaacc    4800
ccccgttcag cccgaccgct gcgccttatc cggtaactat cgtcttgagt ccaacccggt    4860
aagacacgac ttatcgccac tggcagcagc cactggtaac aggattagca gagcgaggta    4920
tgtaggcggt gctacagagt tcttgaagtg gtggcctaac tacggctaca ctagaaggac    4980
agtatttggt atctgcgctc tgctgaagcc agttaccttc ggaaaaagag ttggtagctc    5040
ttgatccggc aaacaaacca ccgctggtag cggtggtttt tttgtttgca agcagcagat    5100
tacgcgcaga aaaaaggat ctcaagaaga tcctttgatc ttttctacgg ggtctgacgc    5160
tcagtggaac gaaaactcac gttaagggat tttggtcatg agattatcaa aaaggatctt    5220
cacctagatc cttttaaagg ccggccgcgg ccgccatcgg catttctttt tgcgttttta    5280
tttgttaact gttaattgtc cttgttcaag gatgctgtct ttgacaacag atgttttctt    5340
gcctttgatg ttcagcagga agctcggcgc aaacgttgat tgtttgtctg cgtagaatcc    5400
tctgtttgtc atatagcttg taatcacgac attgtttcct ttcgcttgag gtacagcgaa    5460
gtgtgagtaa gtaaaggtta catcgttagg atcaagatcc attttttaaca caaggccagt    5520
tttgttcagc ggcttgtatg ggccagttaa agaattagaa acataaccaa gcatgtaaat    5580
atcgttagac gtaatgccgt caatcgtcat ttttgatccg cgggagtcag tgaacaggta    5640
ccatttgccg ttcattttaa agacgttcgc gcgttcaatt tcatctgtta ctgtgttaga    5700
tgcaatcagc ggtttcatca cttttttcag tgtgtaatca tcgtttagct caatcatacc    5760
gagagcgccg tttgctaact cagccgtgcg ttttttatcg ctttgcagaa gtttttgact    5820
ttcttgacgg aagaatgatg tgcttttgcc atagtatgct ttgttaaata aagattcttc    5880
gccttggtag ccatcttcag ttccagtgtt tgcttcaaat actaagtatt tgtggccttt    5940
atcttctacg tagtgaggat ctctcagcgt atggttgtcg cctgagctgt agttgccttc    6000
atcgatgaac tgctgtacat tttgatacgt ttttccgtca ccgtcaaaga ttgatttata    6060
atcctctaca ccgttgatgt tcaaagagct gtctgatgct gatacgttaa cttgtgcagt    6120
tgtcagtgtt tgtttgccgt aatgtttacc ggagaaatca gtgtagaata aacgatttt    6180
tccgtcagat gtaaatgtgg ctgaacctga ccattcttgt gtttggtctt ttaggataga    6240
atcatttgca tcgaatttgt cgctgtcttt aaagacgcgg ccagcgtttt tccagctgtc    6300
aatagaagtt tcgccgactt tttgatagaa catgtaaatc gatgtgtcat ccgcattttt    6360
aggatctccg gctaatgcaa agacgatgtg gtagccgtga tagtttgcga cagtgccgtc    6420
agcgttttgt aatggccagc tgtcccaaac gtccaggcct tttgcagaag agatatttt    6480
aattgtggac gaatcaaatt cagaaacttg atattttca ttttttttgct gttcagggat    6540
ttgcagcata tcatggcgtg taatatggga aatgccgtat gtttccttat atggcttttg    6600
gttcgtttct ttcgcaaacg cttgagttgc gcctcctgcc agcagtgcgg tagtaaaggt    6660
taatactgtt gcttgttttg caaacttttt gatgttcatc gttcatgtct ccttttttat    6720
gtactgtgtt agcggtctgc ttcttccagc cctcctgttt gaagatggca agttagttac    6780
gcacaataaa aaaagaccta aaatatgtaa ggggtgacgc caaagtatac actttgccct    6840
ttacacattt taggtcttgc ctgctttatc agtaacaaac ccgcgcgatt tacttttcga    6900
```

```
cctcattcta ttagactctc gtttggattg caactggtct attttcctct tttgtttgat        6960
agaaaatcat aaaaggattt gcagactacg ggcctaaaga actaaaaaat ctatctgttt        7020
cttttcattc tctgtatttt ttatagtttc tgttgcatgg cataaagtt gccttttaa          7080 tcacaattca gaaatatca taatatctca tttcactaaa taatagtgaa cggcaggtat         7140
atgtgatggg ttaaaaagga tcggcggccg ctcgatttaa atc                         7183
```

<210> SEQ ID NO 9
<211> LENGTH: 1029
<212> TYPE: DNA
<213> ORGANISM: Basfia succiniciproducens
<220> FEATURE:
<221> NAME/KEY: misc_feature
<223> OTHER INFORMATION: nucleotide sequence of ldhA-gene from strain DD1

<400> SEQUENCE: 9

```
ttgacaaaat cagtatgttt aaataaggag ctaactatga agttgccgt ttacagtact         60 aaaaattatg atcgcaaaca tctggatttg gcgaataaaa aatttaattt tgagcttcat        120
ttctttgatt ttttacttga tgaacaaacc gcgaaaatgg cggagggcgc cgatgccgtc       180 tgtatttcg tcaatgatga tgcgagccgc ccggtgttaa caaagttggc gcaaatcgga         240
gtgaaaatta tcgctttacg ttgtgccggt tttaataatg tggatttgga ggcggcaaaa       300
gagctgggat taaaagtcgt acgggtgcct gcgtattcgc cggaagccgt tgccgagcat       360
gcgatcggat taatgctgac tttaaaccgc cgtatccata aggcttatca gcgtacccgc       420
gatgcgaatt tttctctgga aggattggtc ggtttttaata tgttcggcaa aaccgccgga      480
gtgattggta cgggaaaaat cggcttggcg gctattcgca ttttaaaagg cttcggtatg       540
gacgttctgg cgttttgatcc tttttaaaaat ccggcggcgg aagcgttggg cgcaaaatat     600
gtcggtttag acgagcttta tgcaaaatcc catgttatca ctttgcattg cccggctacg       660
gcggataatt atcattttatt aaatgaagcg cttttaataa aaatgcgcga cggtgtaatg      720
attattaata ccagccgcgg cgttttaatt gacagccggg cggcaatcga agcgttaaaa       780
cggcagaaaa tcggcgctct cggtatggat gtttatgaaa atgaacggga tttgttttc        840 gaggataaat ctaacgatgt tattacggat gatgtattcc gtcgcctttc ttcctgtcat       900
aatgtgcttt ttaccggtca tcaggcgttt ttaacgaaag aagcgctgaa taatatcgcc       960
gatgtgactt tatcgaatat tcaggcggtt tccaaaaatg caacgtgcga aaatagcgtt       1020
gaaggctaa                                                              1029
```

<210> SEQ ID NO 10
<211> LENGTH: 342
<212> TYPE: PRT
<213> ORGANISM: Basfia succiniciproducens
<220> FEATURE:
<221> NAME/KEY: MISC_FEATURE
<223> OTHER INFORMATION: amino acid sequence of LdhA from strain DD1

<400> SEQUENCE: 10

```
Met Thr Lys Ser Val Cys Leu Asn Lys Glu Leu Thr Met Lys Val Ala
1               5                   10                  15

Val Tyr Ser Thr Lys Asn Tyr Asp Arg Lys His Leu Asp Leu Ala Asn
                20                  25                  30

Lys Lys Phe Asn Phe Glu Leu His Phe Phe Asp Phe Leu Leu Asp Glu
            35                  40                  45

Gln Thr Ala Lys Met Ala Glu Gly Ala Asp Ala Val Cys Ile Phe Val
```

```
            50                  55                  60
Asn Asp Asp Ala Ser Arg Pro Val Leu Thr Lys Leu Ala Gln Ile Gly
 65                  70                  75                  80

Val Lys Ile Ile Ala Leu Arg Cys Ala Gly Phe Asn Asn Val Asp Leu
                 85                  90                  95

Glu Ala Ala Lys Glu Leu Gly Leu Lys Val Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270

Glu Asn Glu Arg Asp Leu Phe Phe Glu Asp Lys Ser Asn Asp Val Ile
        275                 280                 285

Thr Asp Asp Val Phe Arg Arg Leu Ser Ser Cys His Asn Val Leu Phe
290                 295                 300

Thr Gly His Gln Ala Phe Leu Thr Glu Glu Ala Leu Asn Asn Ile Ala
305                 310                 315                 320

Asp Val Thr Leu Ser Asn Ile Gln Ala Val Ser Lys Asn Ala Thr Cys
                325                 330                 335

Glu Asn Ser Val Glu Gly
            340

<210> SEQ ID NO 11
<211> LENGTH: 741
<212> TYPE: DNA
<213> ORGANISM: Basfia succiniciproducens
<220> FEATURE:
<221> NAME/KEY: misc_feature
<223> OTHER INFORMATION: nucleotide sequence of pflA-gene from strain
      DD1

<400> SEQUENCE: 11
atgtcggttt taggacgaat tcattcattt gaaacctgcg ggacagttga cgggccggga      60
atccgcttta tttattttt acaaggctgc ttaatgcgtt gtaaatactg ccataataga     120
gacacctggg atttgcacgg cggtaaagaa atttccgttg aagaattaat gaaagaagtg     180
gtgacctatc gccatttat gaacgcctcg ggcggcggag ttaccgcttc ggcggtgaa      240 gctattttac aggcggaatt tgtacgggac tggttcagag cctgccataa agaaggaatt     300
aatacttgct tggataccaa cggtttcgtc cgtcatcatg atcatattat tgatgaattg     360
```

```
attgatgaca cggatcttgt gttgcttgac ctgaaagaaa tgaatgaacg ggttcacgaa    420
agcctgattg gcgtgccgaa taaaagagtg ctcgaattcg caaatatttt agcggatcga    480
aatcagcgta cctggatccg ccatgttgta gtgccgggtt atacagatag tgacgaagat    540
ttgcacatgc tggggaattt cattaaagat atgaagaata tcgaaaaagt ggaattatta    600
ccttatcacc gtctaggcgc ccataaatgg gaagtactcg gcgataaata cgagcttgaa    660
gatgtaaaac cgccgacaaa agaattaatg gagcatgtta aggggttgct tgcaggctac    720
gggcttaatg tgacatatta g                                              741
```

<210> SEQ ID NO 12
<211> LENGTH: 246
<212> TYPE: PRT
<213> ORGANISM: Basfia succiniciproducens
<220> FEATURE:
<221> NAME/KEY: MISC_FEATURE
<223> OTHER INFORMATION: amino acid sequence of PflA from strain DD1

<400> SEQUENCE: 12

```
Met Ser Val Leu Gly Arg Ile His Ser Phe Glu Thr Cys Gly Thr Val
1               5                   10                  15

Asp Gly Pro Gly Ile Arg Phe Ile Leu Phe Leu Gln Gly Cys Leu Met
            20                  25                  30

Arg Cys Lys Tyr Cys His Asn Arg Asp Thr Trp Asp Leu His Gly Gly
        35                  40                  45

Lys Glu Ile Ser Val Glu Glu Leu Met Lys Glu Val Val Thr Tyr Arg
    50                  55                  60

His Phe Met Asn Ala Ser Gly Gly Val Thr Ala Ser Gly Gly Glu
65              70                  75                  80

Ala Ile Leu Gln Ala Glu Phe Val Arg Asp Trp Phe Arg Ala Cys His
                85                  90                  95

Lys Glu Gly Ile Asn Thr Cys Leu Asp Thr Asn Gly Phe Val Arg His
            100                 105                 110

His Asp His Ile Ile Asp Glu Leu Ile Asp Asp Thr Asp Leu Val Leu
        115                 120                 125

Leu Asp Leu Lys Glu Met Asn Glu Arg Val His Glu Ser Leu Ile Gly
    130                 135                 140

Val Pro Asn Lys Arg Val Leu Glu Phe Ala Lys Tyr Leu Ala Asp Arg
145                 150                 155                 160

Asn Gln Arg Thr Trp Ile Arg His Val Val Pro Gly Tyr Thr Asp
                165                 170                 175

Ser Asp Glu Asp Leu His Met Leu Gly Asn Phe Ile Lys Asp Met Lys
            180                 185                 190

Asn Ile Glu Lys Val Glu Leu Leu Pro Tyr His Arg Leu Gly Ala His
        195                 200                 205

Lys Trp Glu Val Leu Gly Asp Lys Tyr Glu Leu Glu Asp Val Lys Pro
    210                 215                 220

Pro Thr Lys Glu Leu Met Glu His Val Lys Gly Leu Leu Ala Gly Tyr
225                 230                 235                 240

Gly Leu Asn Val Thr Tyr
                245
```

<210> SEQ ID NO 13
<211> LENGTH: 2313
<212> TYPE: DNA
<213> ORGANISM: Basfia succiniciproducens

```
<220> FEATURE:
<221> NAME/KEY: misc_feature
<223> OTHER INFORMATION: nucleotide sequence of pflD-gene from strain
      DD1

<400> SEQUENCE: 13
atggctgaat taacagaagc tcaaaaaaaa gcatgggaag gattcgttcc cggtgaatgg      60
caaaacggcg taaatttacg tgactttatc caaaaaaact atactccgta tgaaggtgac     120
gaatcattct tagctgatgc gactcctgca accagcgagt tgtggaacag cgtgatggaa     180
ggcatcaaaa tcgaaaacaa aactcacgca cctttagatt tcgacgaaca tactccgtca     240
actatcactt ctcacaagcc tggttatatc aataaagatt tagaaaaaat cgttggtctt     300
caaacagacg ctccgttaaa acgtgcaatt atgccgtacg gcggtatcaa aatgatcaaa     360
ggttcttgcg aagtttacgg tcgtaaatta gatccgcaag tagaatttat tttcaccgaa     420
tatcgtaaaa cccataacca aggcgtattc gacgtttata cgccggatat tttacgctgc     480
cgtaaatcag gcgtgttaac cggtttaccg gatgcttacg gtcgtggtcg tattatcggt     540
gactaccgtc gtttagcggt atacggtatt gattacctga tgaaagataa aaaagcccaa     600
ttcgattcat tacaaccgcg tttggaagcg ggcgaagaca ttcaggcaac tatccaatta     660
cgtgaagaaa ttgccgaaca acaccgcgct ttaggcaaaa tcaaagaaat ggcggcatct     720
tacggttacg acatttccgg ccctgcgaca aacgcacagg aagcaatcca atggacatat     780
tttgcttatc tggcagcggt taaatcacaa aacggtgcgg caatgtcatt cggtcgtacg     840
tctacattct tagatatcta tatcgaacgt gacttaaaac gcggtttaat cactgaacaa     900
caggcgcagg aattaatgga ccacttagta atgaaattac gtatggttcg tttcttacgt     960
acgccggaat acgatcaatt attctcaggc gacccgatgt gggcaaccga aactatcgcc    1020
ggtatgggct tagacggtcg tccgttggta actaaaaaca gcttccgcgt attacatact    1080
ttatacacta tgggtacttc tccggaacca aacttaacta ttctttggtc cgaacaatta    1140
cctgaagcgt tcaaacgttt ctgtgcgaaa gtatctattg atacttcctc cgtacaatac    1200
gaaaatgatg acttaatgcg tcctgacttc aacaacgatg actatgcaat cgcatgctgc    1260
gtatcaccga tggtcgtagg taaacaaatg caattcttcg gtgcgcgcgc aaacttagct    1320
aaaactatgt tatacgcaat taacggcggt atcgatgaga aaaatggtat gcaagtcggt    1380
cctaaaactg cgccgattac agacgaagta ttgaatttcg ataccgtaat cgaacgtatg    1440
gacagtttca tggactggtt ggcgactcaa tatgtaaccg cattgaacat catccacttc    1500
atgcacgata aatatgcata tgaagcggca ttgatggcgt tccacgatcg cgacgtattc    1560
cgtacaatgg cttgcggtat cgcgggtctt tccgtggctg cggactcatt atccgcaatc    1620
aaatatgcga aagttaaacc gattcgcggc gacatcaaag ataaagacgg taatgtcgtg    1680
gcctcgaatg ttgctatcga cttcgaaatt gaaggcgaat atccgcaatt cggtaacaat    1740
gatccgcgtg ttgatgattt agcggtagac ttagttgaac gtttcatgaa aaaagttcaa    1800
aaacacaaaa cttaccgcaa cgcaactccg acacaatcta tcctgactat cacttctaac    1860
gtggtatacg gtaagaaaac cggtaatact ccggacggtc gtcgagcagg cgcgccattc    1920
ggaccgggtg caaacccaat gcacggtcgt gaccaaaaag gtgcggttgc ttcacttact    1980
tctgtggcta aacttccgtt cgcttacgcg aaagacggta tttcatatac cttctctatc    2040
gtaccgaacg cattaggtaa agatgacgaa gcgcaaaaac gcaaccttgc cggtttaatg    2100
gacggttatt tccatcatga agcgacagtg gaaggcggtc aacacttgaa tgttaacgtt    2160
```

```
cttaaccgtg aaatgttgtt agacgcgatg gaaaatccgg aaaaatacccc gcaattaacc    2220 attcgtgttt caggttacgc ggttcgtttc aactcattaa ctaaagagca acaacaagac    2280
gtcatcactc gtacgtttac acaatcaatg taa                                 2313
```

<210> SEQ ID NO 14
<211> LENGTH: 770
<212> TYPE: PRT
<213> ORGANISM: Basfia succiniciproducens
<220> FEATURE:
<221> NAME/KEY: MISC_FEATURE
<223> OTHER INFORMATION: amino acid of PflD from strain DD1

<400> SEQUENCE: 14

```
Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp Glu His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125

Lys Leu Asp Pro Gln Val Glu Phe Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Leu Ala Val Tyr Gly Ile Asp Tyr
            180                 185                 190

Leu Met Lys Asp Lys Lys Ala Gln Phe Asp Ser Leu Gln Pro Arg Leu
        195                 200                 205

Glu Ala Gly Glu Asp Ile Gln Ala Thr Ile Gln Leu Arg Glu Glu Ile
    210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
                245                 250                 255

Gln Trp Thr Tyr Phe Ala Tyr Leu Ala Ala Val Lys Ser Gln Asn Gly
            260                 265                 270

Ala Ala Met Ser Phe Gly Arg Thr Ser Thr Phe Leu Asp Ile Tyr Ile
        275                 280                 285

Glu Arg Asp Leu Lys Arg Gly Leu Ile Thr Glu Gln Gln Ala Gln Glu
    290                 295                 300

Leu Met Asp His Leu Val Met Lys Leu Arg Met Val Arg Phe Leu Arg
305                 310                 315                 320

Thr Pro Glu Tyr Asp Gln Leu Phe Ser Gly Asp Pro Met Trp Ala Thr
                325                 330                 335
```

Glu Thr Ile Ala Gly Met Gly Leu Asp Gly Arg Pro Leu Val Thr Lys
        340                 345                 350

Asn Ser Phe Arg Val Leu His Thr Leu Tyr Thr Met Gly Thr Ser Pro
        355                 360                 365

Glu Pro Asn Leu Thr Ile Leu Trp Ser Glu Gln Leu Pro Glu Ala Phe
        370                 375                 380

Lys Arg Phe Cys Ala Lys Val Ser Ile Asp Thr Ser Ser Val Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Val Val Gly Lys Gln Met Gln Phe
                420                 425                 430

Phe Gly Ala Arg Ala Asn Leu Ala Lys Thr Met Leu Tyr Ala Ile Asn
        435                 440                 445

Gly Gly Ile Asp Glu Lys Asn Gly Met Gln Val Gly Pro Lys Thr Ala
        450                 455                 460

Pro Ile Thr Asp Glu Val Leu Asn Phe Asp Thr Val Ile Glu Arg Met
465                 470                 475                 480

Asp Ser Phe Met Asp Trp Leu Ala Thr Gln Tyr Val Thr Ala Leu Asn
                485                 490                 495

Ile Ile His Phe Met His Asp Lys Tyr Ala Tyr Glu Ala Ala Leu Met
                500                 505                 510

Ala Phe His Asp Arg Asp Val Phe Arg Thr Met Ala Cys Gly Ile Ala
        515                 520                 525

Gly Leu Ser Val Ala Ala Asp Ser Leu Ser Ala Ile Lys Tyr Ala Lys
        530                 535                 540

Val Lys Pro Ile Arg Gly Asp Ile Lys Asp Lys Asp Gly Asn Val Val
545                 550                 555                 560

Ala Ser Asn Val Ala Ile Asp Phe Glu Ile Glu Gly Glu Tyr Pro Gln
                565                 570                 575

Phe Gly Asn Asn Asp Pro Arg Val Asp Asp Leu Ala Val Asp Leu Val
                580                 585                 590

Glu Arg Phe Met Lys Lys Val Gln Lys His Lys Thr Tyr Arg Asn Ala
        595                 600                 605

Thr Pro Thr Gln Ser Ile Leu Thr Ile Thr Ser Asn Val Val Tyr Gly
        610                 615                 620

Lys Lys Thr Gly Asn Thr Pro Asp Gly Arg Arg Ala Gly Ala Pro Phe
625                 630                 635                 640

Gly Pro Gly Ala Asn Pro Met His Gly Arg Asp Gln Lys Gly Ala Val
                645                 650                 655

Ala Ser Leu Thr Ser Val Ala Lys Leu Pro Phe Ala Tyr Ala Lys Asp
                660                 665                 670

Gly Ile Ser Tyr Thr Phe Ser Ile Val Pro Asn Ala Leu Gly Lys Asp
        675                 680                 685

Asp Glu Ala Gln Lys Arg Asn Leu Ala Gly Leu Met Asp Gly Tyr Phe
        690                 695                 700

His His Glu Ala Thr Val Glu Gly Gly Gln His Leu Asn Val Asn Val
705                 710                 715                 720

Leu Asn Arg Glu Met Leu Leu Asp Ala Met Glu Asn Pro Glu Lys Tyr
                725                 730                 735

Pro Gln Leu Thr Ile Arg Val Ser Gly Tyr Ala Val Arg Phe Asn Ser
                740                 745                 750

```
Leu Thr Lys Glu Gln Gln Gln Asp Val Ile Thr Arg Thr Phe Thr Gln
        755                 760                 765
Ser Met
    770
```

MODIFIED MICROORGANISM FOR IMPROVED PRODUCTION OF FINE CHEMICALS ON SUCROSE

This application is a National Stage application of International Application No. PCT/EP2015/052380, filed Feb. 5, 2015, which claims priority under 35 U.S.C. §119 to European Patent Application No. 14154288.6, filed Feb. 7, 2014.

INCORPORATION BY REFERENCE OF MATERIAL SUBMITTED ELECTRONICALLY

This application incorporates by reference in its entirety a computer-readable nucleotide/amino acid sequence listing identified as one 66,281 byte ASCII (text) file named "H74821_SeqListing.txt," created Jul. 29, 2016.

The present invention relates to a modified microorganism, to a method for producing organic compounds and to the use of modified microorganisms.

Organic compounds such as small dicarboxylic acids having 6 or fewer carbons are commercially significant chemicals with many uses. For example, the small diacids include 1,4-diacids, such as succinic acid, malic acid and tartaric acid, and the 5-carbon molecule itaconic acid. Other diacids include the two carbon oxalic acid, three carbon malonic acid, five carbon glutaric acid and the 6 carbon adipic acid and there are many derivatives of such diacids as well.

As a group the small diacids have some chemical similarity and their uses in polymer production can provide specialized properties to the resin. Such versatility enables them to fit into the downstream chemical infrastructure markets easily. For example, the 1,4-diacid molecules fulfill many of the uses of the large scale chemical maleic anhydride in that they are converted to a variety of industrial chemicals (tetrahydrofuran, butyrolactone, 1,4-butanediol, 2-pyrrolidone) and the succinate derivatives succindiamide, succinonitrile, diaminobutane and esters of succinate. Tartaric acid has a number of uses in the food, leather, metal and printing industries. Itaconic acid forms the starting material for production of 3-methylpyrrolidone, methyl-BDO, methyl-THF and others.

In particular, succinic acid or succinate—these terms are used interchangeably herein—has drawn considerable interest because it has been used as a precursor of many industrially important chemicals in the food, chemical and pharmaceutical industries. In fact, a report from the U.S. Department of Energy reports that succinic acid is one of 12 top chemical building blocks manufactured from biomass. Thus, the ability to make diacids in bacteria would be of significant commercial importance.

WO-A-2009/024294 discloses a succinic acid producing bacterial strain, being a member of the family of Pasteurellaceae, originally isolated from rumen, and capable of utilizing glycerol as a carbon source and variant and mutant strains derived there from retaining said capability, in particular, a bacterial strain designated DD1 as deposited with DSMZ (Deutsche Sammlung von Mikroorganismen and Zellkulturen GmbH, Inhoffenstr. 7B, D-38124 Braunschweig, Germany) having the deposit number DSM 18541 (ID 06-614) and having the ability to produce succinic acid. The DD1-strain belongs to the species *Basfia succiniciproducens* and the family of Pasteurellaceae as classified by Kuhnert et al., 2010. Mutations of these strains, in which the ldhA-gene and/or the pflD- or the pflA-gene have been disrupted, are disclosed in WO-A-2010/092155, these mutant strains being characterized by a significantly increased production of succinic acid from carbon sources such as glycerol or mixtures of glycerol and carbohydrates such as maltose, under anaerobic conditions compared to the DD1-wild-type disclosed in WO-A-2009/024294.

However, bio-based succinate still faces the challenge of becoming cost competitive against petrochemical-based alternatives. In order to develop the bio-based industrial production of succinic acid, it will be important to grow the cells in a low cost medium, and the working strain optimally should be able to metabolize a wide range of low-cost sugar feedstock to produce succinic acid in good yields so that the cheapest available raw materials can be used.

Sucrose (commonly known as sugar) is a disaccharide consisting of glucose and fructose, and it is a carbon source that is very abundant in nature and is produced from all plants having photosynthesis ability. Particularly, sugarcane and sugar beet contain large amounts of sucrose, and more than 60% of the world's sucrose is currently being produced from sugarcane. Particularly, sucrose is produced at a very low cost, because it can be industrially produced through a simple process of evaporating/concentrating extracts obtained by mechanical pressing of sugarcanes. Sucrose as a raw material for producing chemical compounds through microbial fermentation is thus inexpensive and it also functions to protect the cell membrane from an external environment containing large amounts of desired metabolites, thus producing high-concentrations of desired metabolites as shown by Kilimann et al. (*Biochimica et Biophysica Acta*, 1764, 2006).

Even though sucrose is an excellent raw material having the above-described advantages, including low price and a function to protect microorganisms from an external environment, the disadvantage of this carbon source can be seen in the fact a large number of microorganisms do not have a complete mechanism of transporting sucrose into cell, degrading the transported sucrose and linking the degraded products to glycolysis, and thus cannot use sucrose as a carbon source. Even in the case of microorganisms having a mechanism capable of using sucrose, they cannot efficiently produce desired metabolites, because the rate of ingestion and degradation of sucrose as a carbon source is very low.

It was therefore an object of the present invention to overcome the disadvantages of the prior art.

In particular, it was an object of the present invention to provide microorganisms which can be used for the fermentative production of organic compounds such as succinic acid and that can efficiently utilize sucrose as the predominant carbon source without sacrificing growth rates or yields. Preferably said microorganisms would be able to use a number of low cost carbon sources and produce excellent yields of organic compounds such as succinic acid. Compared to the recombinant microorganisms of the prior art that are used for the fermentative production of succinic acid, the microorganisms of the present invention should be characterized by an increased succinic acid yield and an increased carbon yield during growth of the cells on sucrose as the predominant carbon source.

A contribution to achieving the abovementioned aims is provided by a modified microorganism having, compared to its wild-type, a reduced activity of the enzyme that is encoded by the fruA-gene, wherein the wild-type from which the modified microorganism has been derived belongs to the family of Pasteurellaceae. A contribution to achieving the abovementioned aims is in particular provided by a modified microorganism in which the fruA-gene or parts thereof have been deleted, wherein the wild-type from which the modified microorganism has been derived belongs to the family of Pasteurellaceae.

Surprisingly, it has been discovered that a reduction of the activity of the enzyme that is encoded by the fruA-gene (this enzyme presumably being a fructose-specific phosphotransferase), for example by a deletion of the fruA-gene, results in a modified Pasteurellaceae-strain that, compared to the corresponding microorganism in which the activity of this enzyme has not been decreased, is characterized by an increased yield of organic compounds such as succinic acid, especially if these modified microorganisms are grown on sucrose as the assimilable carbon source. This is indeed surprising as according to the teaching in Lee et al. (Applied and Environmental Microbiology (2010), Vol. 76(5), p. 1699-1703)) at least in Mannheimia succiniciproducens the fruA-gene encodes for a fructose PTS-system that is responsible for the uptake of fructose into the cells. When Mannheimi succiniciproducens in cultured on sucrose, the disaccharide is hydrolyzed inside the cell to obtain glucose-6-phosphat and fructose. Fructose, however, is secreted after hydrolysis and is taken up again by the cell using the fructose PTS-system. The person skilled in the art would therefore have assumed that an inactivation of the fruA-gene would lead to a decreased formation of succinic acid when the cells are cultured on sucrose as the predominant carbon source as at least a part of the disaccharide (i. e. fructose) can not be imported into the cell.

In context with the expression "a modified microorganism having, compared to its wild-type, a reduced activity of the enzyme that is encoded by the x-gene", wherein the x-gene is the fruA-gene and optionally, as described later, the ldhA-gene, the pflA-gene and/or the pflD-gene, the term "wild-type" refers to a microorganism in which the activity of the enzyme that is encoded by the x-gene has not been decreased, i. e. to a microorganism whose genome is present in a state as before the introduction of a genetic modification of the x-gene (in particular of the fruA-gene and optionally the ldhA-gene, the pflA-gene and/or the pflD-gene). Preferably, the expression "wild-type" refers to a microorganism whose genome, in particular whose x-gene, is present in a state as generated naturally as the result of evolution. The term may be used both for the entire microorganism but preferably for individual genes, e.g. the fruA-gene, the ldhA-gene, the pflA-gene and/or the pflD-gene. The term "modified microorganism" thus includes a microorganism which has been genetically altered, modified or engineered (e.g., genetically engineered) such that it exhibits an altered, modified or different genotype and/or phenotype (e. g., when the genetic modification affects coding nucleic acid sequences of the microorganism) as compared to the naturally-occurring wild-type microorganism from which it was derived. According to a particular preferred embodiment of the modified microorganism according to the present invention the modified microorganism is a recombinant microorganism, which means that the microorganism has been obtained using recombinant DNA. The expression "recombinant DNA" as used herein refers to DNA sequences that result from the use of laboratory methods (molecular cloning) to bring together genetic material from multiple sources, creating sequences that would not otherwise be found in biological organisms. An example of such a recombinant DNA is a plasmid into which a heterologous DNA-sequence has been inserted.

The wild-type from which the microorganism according to the present invention are derived belongs to the family of Pasteurellaceae. Pasteurellaceae comprise a large family of Gramnegative Proteobacteria with members ranging from bacteria such as *Haemophilus influenzae* to commensals of the animal and human mucosa. Most members live as commensals on mucosal surfaces of birds and mammals, especially in the upper respiratory tract. Pasteurellaceae are typically rod-shaped, and are a notable group of facultative anaerobes. They can be distinguished from the related Enterobacteriaceae by the presence of oxidase, and from most other similar bacteria by the absence of flagella. Bacteria in the family Pasteurellaceae have been classified into a number of genera based on metabolic properties and there sequences of the 16S RNA and 23S RNA. Many of the Pasteurellaceae contain pyruvate-formate-lyase genes and are capable of anaerobically fermenting carbon sources to organic acids.

According to a particular preferred embodiment of the modified microorganism according to the present invention the wild-type from which the modified microorganism has been derived belongs to the genus *Basfia* and it is particularly preferred that the wild-type from which the modified microorganism has been derived belongs to the species *Basfia succiniciproducens.*

Most preferably, the wild-type from which the modified microorganism according to the present invention as been derived is *Basfia succiniciproducens*-strain DD1 deposited under the Budapest Treaty with DSMZ (Deutsche Sammlung von Mikroorganismen and Zellkulturen, GmbH), Germany, having the deposit number DSM 18541. This strain has been originally isolated from the rumen of a cow of German origin. *Pasteurella* bacteria can be isolated from the gastrointestinal tract of animals and, preferably, mammals. The bacterial strain DD1, in particular, can be isolated from bovine rumen and is capable of utilizing glycerol (including crude glycerol) as a carbon source. Further strains of the genus *Basfia* that can be used for preparing the modified microorganism according to the present invention are the *Basfia*-strain that has been deposited under the deposit number DSM 22022 or the *Basfia*-strains that have been deposited with the Culture Collection of the University of Göteborg (CCUG), Sweden, having the deposit numbers CCUG 57335, CCUG 57762, CCUG 57763, CCUG 57764, CCUG 57765 or CCUG 57766. Said strains have been originally isolated from the rumen of cows of German or Swiss origin.

In this context it is particularly preferred that the wild-type from which the modified microorganism according to the present invention has been derived has a 16S rDNA of SEQ ID NO: 1 or a sequence, which shows a sequence homology of at least 96%, at least 97%, at least 98%, at least 99% or at least 99.9% with SEQ ID NO: 1. It is also preferred that the wild-type from which the modified microorganism according to the present invention has been derived has a 23S rDNA of SEQ ID NO: 2 or a sequence, which shows a sequence homology of at least 96%, at least 97%, at least 98%, at least 99% or at least 99.9% with SEQ ID NO: 2.

The identity in percentage values referred to in connection with the various polypeptides or polynucleotides to be used for the modified microorganism according to the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0, http://emboss.source-forge.net/what/) with the default parameters which are, i.e. gap open (penalty to open a gap):

10.0, gap extend (penalty to extend a gap): 0.5, and data file (scoring matrix file included in package): EDNAFUL.

It should be noted that the modified microorganism according to the present invention can not only be derived from the above mentioned wild-type-microorganisms, especially from *Basfia succiniciproducens*-strain DD1, but also from variants of these strains. In this context the expression "a variant of a strain" comprises every strain having the same or essentially the same characteristics as the wild-type-strain. In this context it is particularly preferred that the 16 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wild-type from which the variant has been derived. It is also particularly preferred that the 23 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wild-type from which the variant has been derived. A variant of a strain in the sense of this definition can, for example, be obtained by treating the wild-type-strain with a mutagenizing chemical agent, X-rays, or UV light.

The modified microorganism according to the present invention is characterized in that, compared to its wild-type, the activity of the enzyme that is encoded by the fruA-gene is reduced.

The reduction of the enzyme activity ($\Delta_{activity}$) is defined as follows:

$$\Delta_{activity} = 100\% - \left(\frac{\text{activity of the modified microorganism}}{\text{activity of the wildtype}} \times 100\%\right)$$

wherein, when determining $\Delta_{activity}$, the activity in the wild-type and the activity in the modified microorganism are determined under exactly the same conditions. Methods for the detection and determination of the activity of the enzyme that is encoded by the fruA-gene can be found, for example, in the above referenced publication of Lee et al.

The reduced activity of the enzymes disclosed herein, in particular the reduced activity of the enzyme encoded by the fruA-gene, the lactate dehydrogenase and/or the pyruvate formate lyase, can be a reduction of the enzymatic activity by at least 50%, compared to the activity of said enzyme in the wild-type of the microorganism, or a reduction of the enzymatic activity by at least 90%, or more preferably a reduction of the enzymatic activity by at least 95%, or more preferably a reduction of the enzymatic activity by at least 98%, or even more preferably a reduction of the enzymatic activity by at least 99% or even more preferably a reduction of the enzymatic activity by at least 99.9%. The term "reduced activity of the enzyme that is encoded by the fruA-gene" or—as described below—"a reduced lactate dehydrogenase activity" or "a reduced pyruvate formate lyase activity", also encompasses a modified microorganism which has no detectable activity of these enzymes.

The term "reduced activity of an enzyme" includes, for example, the expression of the enzyme by said genetically manipulated (e.g., genetically engineered) microorganism at a lower level than that expressed by the wild-type of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

Microorganisms having a reduced activity of the enzyme encoded by the fruA-gene may occur naturally, i.e. due to spontaneous mutations. A microorganism can be modified to lack or to have significantly reduced activity of the enzyme that is encoded by the fruA-gene by various techniques, such as chemical treatment or radiation. To this end, microorganisms will be treated by, e.g., a mutagenizing chemical agent, X-rays, or UV light. In a subsequent step, those microorganisms which have a reduced activity of the enzyme that is encoded by the fruA-gene will be selected. Modified microorganisms are also obtainable by homologous recombination techniques which aim to mutate, disrupt or excise the fruA-gene in the genome of the microorganism or to substitute the gene with a corresponding gene that encodes for an enzyme which, compared to the enzyme encoded by the wild-type-gene, has a reduced activity.

According to a preferred embodiment of the modified microorganism according to the present invention, a reduction of the activity of the enzyme encoded by the fruA-gene is achieved by a modification of the fruA-gene, wherein this gene modification is preferably realized by a deletion of the fruA-gene or at least a part thereof, a deletion of a regulatory element of the fruA-gene or parts thereof, such as a promotor sequence, or by an introduction of at least one mutation into the fruA-gene.

In the following, a suitable technique for recombination, in particular for introducing a mutation or for deleting sequences, is described.

This technique is also sometimes referred to as the "Campbell recombination" herein (Leen-houts et al., *Appl Env Microbiol*. (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in"

transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

The fruA-gene the activity of which is reduced in the modified microorganism according to the present invention preferably comprises a nucleic acid selected from the group consisting of:
a) nucleic acids having the nucleotide sequence of SEQ ID NO: 3;
b) nucleic acids encoding the amino acid sequence of SEQ ID NO: 4;
c) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a) or b), the identity being the identity over the total length of the nucleic acids of a) or b);
d) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of a) or b), the identity being the identity over the total length of amino acid sequence encoded by the nucleic acids of a) or b);
e) nucleic acids capable of hybridizing under stringent conditions with a complementary sequence of any of the nucleic acids according to a) or b); and
f) nucleic acids encoding the same protein as any of the nucleic acids of a) or b), but differing from the nucleic acids of a) or b) above due to the degeneracy of the genetic code.

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature". The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985)). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50°

C. with washing in 2×SSC, 0.1% SDS at 50° C. or 65° C., preferably at 65° C., with a specific nucleic acid molecule (DNA; RNA; ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole fruA nucleic acids. Alternatively, preferred hybridization conditions encompass hybridization at 65° C. in 1×SSC or at 42° C. in 1×SSC and 50% formamide, followed by washing at 65° C. in 0.3×SSC or hybridization at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The fruA-gene or parts of which that may be deleted by the above mentioned "Campbell recombination" or in which at least one mutation is introduced by the above mentioned "Campbell recombination" preferably comprises a nucleic acid as defined above.

Nucleic acid having the nucleotide sequence of SEQ ID NO: 3 corresponds to the fruA-gene of *Basfia succiniciproducens*-strain DD1.

According to a preferred embodiment of the modified microorganism according to the present invention, the modified microorganism is not characterized by a sucrose-mediated catabolic repression of glycerol. Microorganisms showing a sucrose-mediated catabolic repression of glycerol are, for example, disclosed in WO-A-2012/030130. Furthermore, it is preferred that in the modified microorganism according to the present invention at least one gene selected from the group consisting of the pta-gene and the ackA-gene is not deleted. Preferably, neither the ptA-gene nor the ackA-gene is deleted. In this context it is particularly preferred that in the modified microorganism of the present invention the activity of the enzyme encoded by the pta-gene (which is a phosphotransacetylase), the activity of the enzyme encoded by the ackA-gene (which is a acetate kinase) or the activity of the enzyme encoded by the pta-gene and the activity of the enzyme encoded by the ackA-gene is/are not reduced compared to the corresponding activity of this enzyme/these enzymes in the wild-type.

According to a further preferred embodiment of the modified microorganism according to the present invention, this microorganism is not only characterized by a reduced activity of the enzyme encoded by the fruA-gene, but also, compared to the wild-type, by
i) a reduced pyruvate formate lyase activity,
ii) a reduced lactate dehydrogenase activity, or
iii) a reduced pyruvate formate lyase activity and a reduced lactate dehydrogenase activity.

Modified microorganisms being deficient in lactate dehydrogenase and/or being deficient in pyruvate formate lyase activity are disclosed in WO-A-2010/092155, US 2010/0159543 and WO-A-2005/052135, the disclosure of which with respect to the different approaches of reducing the activity of lactate dehydrogenase and/or pyruvate formate lyase in a microorganism, preferably in a bacterial cell of the genus *Pasteurella*, particular preferred in *Basfia succiniciproducens* strain DD1, is incorporated herein by reference. Methods for determining the pyruvate formate lyase activity are, for example, disclosed by Asanum N. and Hino T. in "*Effects of pH and Energy Supply on Activity and Amount of Pyruvate-Formate-Lyase in Streptococcus bovis*", Appl. Environ. Microbiol. (2000), Vol. 66, pages 3773-3777 and methods for determining the lactate dehydrogenase activity are, for example, disclosed by Bergmeyer, H. U., Bergmeyer J. and Grassi, M. (1983-1986) in "*Methods of Enzymatic Analysis*", 3$^{rd}$ Edition, Volume III, pages 126-133, Verlag Chemie, Weinheim In this context it is preferred that the reduction of the activity of lactate dehydrogenase is achieved by an inactivation of the ldhA-gene (which encodes the lactate dehydrogenase; LdhA; EC 1.1.1.27 or EC 1.1.1.28) and the reduction of the pyruvate formate lyase is achieved by an inactivation of the pflA-gene (which encodes for an activator of pyruvate formate lyase; PflA; EC 1.97.1.4) or the pflD-gene (which encodes the pyruvate formate lyase; PflD; EC 2.3.1.54), wherein the inactivation of these genes (i. e. ldhA, pflA and pflD) is preferably achieved by a deletion of theses genes or parts thereof, by a deletion of a regulatory element of these genes or at least a part thereof or by an introduction of at least one mutation into these genes, wherein these modifications are preferably performed by means of the "Campbell recombination" as described above.

The ldhA-gene the activity of which is reduced in the modified microorganism according to the present invention preferably comprises a nucleic acid selected from the group consisting of:
α1) nucleic acids having the nucleotide sequence of SEQ ID NO: 9;
α2) nucleic acids encoding the amino acid sequence of SEQ ID NO: 10;
α3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of α1) or α2), the identity being the identity over the total length of the nucleic acids of α1) or α2);
α4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of α1) or α2), the identity being the identity over the total length of amino acid sequence encoded by the nucleic acids of α1) or α2);
α5) nucleic acids capable of hybridizing under stringent conditions with a complementary sequence of any of the nucleic acids according to α1) or α2); and
α6) nucleic acids encoding the same protein as any of the nucleic acids of α1) or α2), but differing from the nucleic acids of α1) or α2) above due to the degeneracy of the genetic code.

The pflA-gene the activity of which is reduced in the modified microorganism according to the present invention preferably comprises a nucleic acid selected from the group consisting of:
β1) nucleic acids having the nucleotide sequence of SEQ ID NO: 11;
β2) nucleic acids encoding the amino acid sequence of SEQ ID NO: 12;
β3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of β1)

or β2), the identity being the identity over the total length of the nucleic acids of β1) or β2);

β4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of β1) or β2), the identity being the identity over the total length of amino acid sequence encoded by the nucleic acids of β1) or β2)

β5) nucleic acids capable of hybridizing under stringent conditions with a complementary sequence of any of the nucleic acids according to β1) or β2); and β6) nucleic acids encoding the same protein as any of the nucleic acids of β1) or β2), but differing from the nucleic acids of β1) or β2) above due to the degeneracy of the genetic code.

The pflD-gene the activity of which is reduced in the modified microorganism according to the present invention preferably comprises a nucleic acid selected from the group consisting of:

γ1) nucleic acids having the nucleotide sequence of SEQ ID NO: 13;

γ2) nucleic acids encoding the amino acid sequence of SEQ ID NO: 14;

γ3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of γ1) or γ2), the identity being the identity over the total length of the nucleic acids of γ1) or γ2);

γ4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of γ1) or γ2), the identity being the identity over the total length of amino acid sequence encoded by the nucleic acids of γ1) or γ2);

γ5) nucleic acids capable of hybridizing under stringent conditions with a complementary sequence of any of the nucleic acids according to γ1) or γ2); and γ6) nucleic acids encoding the same protein as any of the nucleic acids of γ1) or γ2), but differing from the nucleic acids of γ1) or γ2) above due to the degeneracy of the genetic code.

In this context it is preferred that the modified microorganism according to the present invention further comprises:

A) a deletion of the ldhA-gene or at least a part thereof, a deletion of a regulatory element of the ldhA-gene or at least a part thereof or an introduction of at least one mutation into the ldhA-gene;

B) a deletion of the pflD-gene or at least a part thereof, a deletion of a regulatory element of the pflD-gene or at least a part thereof or an introduction of at least one mutation into the pflD-gene;

C) a deletion of the pflA-gene or at least a part thereof, a deletion of a regulatory element of the pflA-gene or at least a part thereof or an introduction of at least one mutation into the pflA-gene;

D) a deletion of the ldhA-gene or at least a part thereof, a deletion of a regulatory element of the ldhA-gene or at least a part thereof or an introduction of at least one mutation into the ldhA-gene and a deletion of the pflD-gene or at least a part thereof, a deletion of a regulatory element of the pflD-gene or at least a part thereof or an introduction of at least one mutation into the pflD-gene;

or

E) a deletion of the ldhA-gene or at least a part thereof, a deletion of a regulatory element of the ldhA-gene or at least a part thereof or an introduction of at least one mutation into the ldhA-gene and a deletion of the pflA-gene or at least a part thereof, a deletion of a regulatory element of the pflA-gene or at least a part thereof or an introduction of at least one mutation into the pflA-gene.

Particular preferred embodiments of the modified microorganisms according to the present invention are:

modified bacterial cells of the genus *Basfia* and particular preferred of the species *Basfia succiniciproducens*, in which the fruA-gene or at least a part thereof has been deleted or wherein at least one mutation has been introduced in the fruA-gene, wherein it is further preferred that the modified bacterial cell is not characterized by a sucrose-mediated catabolic repression of glycerol;

modified bacterial cells of the genus *Basfia* and particular preferred of the species *Basfia succiniciproducens*, in which the fruA-gene or at least a part thereof has been deleted or wherein at least one mutation has been introduced in the fruA-gene, and in which, compared to the wild-type, the activity of the lactate dehydrogenase is reduced, preferably by a modification of the ldhA-gene, in particular by a modification of the ldhA-gene having the nucleic acid sequence according to SEQ ID NO: 9 and encoding for LdhA having the amino acid sequence according to SEQ ID NO: 10, wherein it is further preferred that the modified microorganism is not characterized by a sucrose-mediated catabolic repression of glycerol;

modified bacterial cells of the genus *Basfia* and particular preferred of the species *Basfia succiniciproducens*, in which the fruA-gene or at least a part thereof has been deleted or wherein at least one mutation has been introduced in the fruA-gene and in which, compared to the wild-type, the activity of the pyruvate formate lyase is reduced, preferably by a modification of the pflA-gene or the pflD-gene, in particular by a modification of the pflA-gene having the nucleic acid sequence according to SEQ ID NO: 11 and encoding for PflA having the amino acid sequence according to SEQ ID NO: 12 or by a modification of the pflD-gene having the nucleic acid sequence according to SEQ ID NO: 13 and encoding for PflD having the amino acid sequence according to SEQ ID NO: 14, wherein it is further preferred that the modified bacterial cell is not characterized by a sucrose-mediated catabolic repression of glycerol;

modified bacterial cells of the genus *Basfia* and particular preferred of the species *Basfia succiniciproducens*, in which the fruA-gene or at least a part thereof has been deleted or wherein at least one mutation has been introduced in the fruA-gene and in which, compared to the wild-type, the activity of the lactate dehydrogenase and the pyruvate formate lyase is reduced, preferably by a modification of the ldhA-gene and the pflA-gene, in particular by a modification of the ldhA-gene having the nucleic acid sequence according to SEQ ID NO: 9 and encoding for LdhA having the amino acid sequence according to SEQ ID NO: 10 or by a modification of the pflA-gene having the nucleic acid sequence according to SEQ ID NO: 11 and encoding for PflA having the amino acid sequence according to SEQ ID NO: 12, or a modification of the ldhA-gene and the pflD-gene, in particular by a modification of the ldhA-gene having the nucleic acid sequence according to SEQ ID NO: 9 and encoding for LdhA having the amino acid sequence according to SEQ ID NO: 10 or by a modification of the pflD-gene having the nucleic acid sequence according to SEQ ID NO: 13 and encoding for PflD having the amino acid sequence according to SEQ ID NO: 14, wherein it is further preferred that the modified bacterial cell is not characterized by a sucrose-mediated catabolic repression of glycerol.

A contribution to solving the problems mentioned at the outset is furthermore provided by a method of producing an organic compound comprising:

I) cultivating the modified microorganism according to the present invention in a culture medium comprising sucrose as an assimilable carbon source to allow the modified microorganism to produce the organic compound, thereby obtaining a fermentation broth comprising the organic compound;

II) recovering the organic compound from the fermentation broth obtained in process step I).

In process step I) the modified microorganism according to the present invention is cultured in a culture medium comprising sucrose as the assimilable carbon source to allow the modified microorganism to produce the organic compound, thereby obtaining a fermentation broth comprising the organic compound. Preferred organic compounds that can be produced by the process according to the present invention comprise carboxylic acids such as formic acid, lactic acid, propionic acid, 2-hydroxypropionic acid, 3-hydroxypropionic acid, 3-hydroxybutyric acid, acrylic acid, pyruvic acid or salts of these carboxylic acids, dicarboxylic acids such as malonic acid, succinic acid, malic acid, tartaric acid, glutaric acid, itaconic acid, adipic acid or salts thereof, tricarboxylic acids such as citric acid or salts thereof, alcohols such as methanol or ethanol, amino acids such as L-asparagine, L-aspartic acid, L-arginine, L-isoleucine, L-glycine, L-glutamine, L-glutamic acid, L-cysteine, L-serine, L-tyrosine, L-tryptophan, L-threonine, L-valine, L-histidine, L-proline, L-methionine, L-lysine, L-leucine, etc.

According to a preferred embodiment of the process according to the present invention the organic compound is succinic acid. The term "succinic acid", as used in the context of the present invention, has to be understood in its broadest sense and also encompasses salts thereof (i. e. succinate), as for example alkali metal salts, like $Na^+$ and $K^+$-salts, or earth alkali salts, like $Mg^{2+}$ and $Ca^{2+}$-salts, or ammonium salts or anhydrides of succinic acid.

The modified microorganism according to the present invention is, preferably, incubated in the culture medium at a temperature in the range of about 10 to 60° C. or 20 to 50° C. or 30 to 45° C. at a pH of 5.0 to 9.0 or 5.5 to 8.0 or 6.0 to 7.0.

Preferably, the organic compound, especially succinic acid, is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The assimilable carbon source is preferably sucrose.

According to a preferred embodiment of the process according to the present invention the assimilable carbon source is not a mixture of glycerol and sucrose. In this context it is preferred that at least 50 wt.-%, preferably at least 75 wt.-%, more preferably at least 90 wt.-%, even more preferably at least 95 wt.-% and most preferably at least 99 wt.-% of the assimilable carbon source, based on the total weight of the assimilable carbon source with the exception of carbon dioxide, is sucrose. It is furthermore preferred that less than 50 wt.-%, preferably less than 25 wt.-%, more preferably less than 10 wt.-%, even more preferably less than 5 wt.-% and most preferably less than 1 wt.-% of the assimilable carbon source, based on the total weight of the assimilable carbon source, is glycerol.

The initial concentration of the assimilable carbon source, preferably the initial concentration of sucrose, is, preferably, adjusted to a value in a range of 5 to 100 g/l, preferably 5 to 75 g/l and more preferably 5 to 50 g/l and may be maintained in said range during cultivation. The pH of the reaction medium may be controlled by addition of suitable bases as for example, gaseous ammonia, $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, CaO, $CH_6N_2O_2$, $C_2H_7N$ and/or mixtures thereof. These alkaline neutralization agents are especially required if the organic compounds that are formed in the course of the fermentation process are carboxylic acids or dicarboxylic acids. In the case of succinic acid as the organic compound, $Mg(OH)_2$ is a particular preferred base.

The fermentation step I) according to the present invention can, for example, be performed in stirred fermenters, bubble columns and loop reactors. A comprehensive overview of the possible method types including stirrer types and geometric designs can be found in Chmiel: "Bio-prozesstechnik: Einführung in die Bioverfahrenstechnik", Volume 1. In the process according to the present invention, typical variants available are the following variants known to those skilled in the art or explained, for example, in Chmiel, Hammes and Bailey: "Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing the organic acid, especially succinic acid, in process step I) are:
Assimilable carbon source: sucrose
Temperature: 30 to 45° C.
pH: 5.5 to 7.0
Supplied gas: $CO_2$ It is furthermore preferred in process step I) that the assimilable carbon source, preferably sucrose, is converted to the organic compound, preferably to succinic acid, with a carbon yield YP/S of at least 0.5 g/g up to about 1.18 g/g; as for example a carbon yield YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g or of at least 1.1 g/g (organic compound/carbon, preferably succinic acid/carbon).

It is furthermore preferred in process step I) that the assimilable carbon source, preferably sucrose, is converted to the organic compound, preferably to succinic acid, with a specific productivity yield of at least 0.6 g g $DCW^{-1}h^{-1}$ organic compound, preferably succinic acid, or of at least of at least 0.65 g g $DCW^{-1}h^{-1}$, of at least 0.7 g g $DCW^{-1}h^{-1}$, of at least 0.75 g g $DCW^{-1}h^{-1}$ or of at least 0.77 g g $DCW^{-1}h^{-1}$ organic compound, preferably succinic acid.

It is furthermore preferred in process step I) that the sucrose is converted to the organic compound, preferably to succinic acid, with a space time yield for the organic compound, preferably for succinic acid, of at least 2.2 g/(L×h) or of at least 2.5 g/(L×h), at least 2.75 g/(L×h), at least 3 g/(L×h), at least 3.25 g/(L×h), at least 3.5 g/(L×h), at least 3.7 g/(L×h), at least 4.0 g/(L×h) at least 4.5 g/(L×h) or at least 5.0 g/(L×h) of the organic compound, preferably succinic acid. According to another preferred embodiment of the process according to the present invention in process step I) the modified microorganism is converting at least 20 g/L, more preferably at least 25 g/l and even more preferably at least 30 g/l sucrose to at least 20 g/l, more preferably to at least 25 g/l and even more preferably at least 30 g/l of the organic compound, preferably succinic acid.

The different yield parameters as described herein ("carbon yield" or "YP/S"; "specific productivity yield"; or "space-time-yield (STY)") are well known in the art and are determined as described for example by Song and Lee, 2006. "Carbon yield" and "YP/S" (each expressed in mass of organic compound produced/mass of assimilable carbon source consumed) are herein used as synonyms. The specific productivity yield describes the amount of a product, like succinic acid, that is produced per h and L fermentation broth per g of dry biomass. The amount of dry cell weight stated as "DCW" describes the quantity of biologically active microorganism in a biochemical reaction. The value is given as g product per g DCW per h (i.e. g g $DCW^{-1}$ $h^{-1}$). The space-time-yield (STY) is defined as the ratio of the total amount of organic compound formed in the fermentation process to the volume of the culture, regarded over the entire time of cultivation. The space-time yield is also known as the "volumetric productivity".

In process step II) the organic compound, preferably succinic acid, is recovered from the fermentation broth obtained in process step I).

Usually, the recovery process comprises the step of separating the recombinant microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the organic compound, preferably succinic acid, is further purified. If, however, the organic compound is converted into a secondary organic product by chemical reactions as described below, a further purification of the organic compound is, depending on the kind of reaction and the reaction conditions, not necessarily required. For the purification of the organic compound obtained in process step II), preferably for the purification of succinic acid, methods known to the person skilled in the art can be used, as for example crystallization, filtration, electrodialysis and chromatography. In the case of succinic acid as the organic compound, for example, succinic acid may be isolated by precipitating it as a calcium succinate product by using calcium hydroxide, -oxide, -carbonate or hydrogen carbonate for neutralization and filtration of the precipitate. The succinic acid is recovered from the precipitated calcium succinate by acidification with sulfuric acid followed by filtration to remove the calcium sulfate (gypsum) which precipitates. The resulting solution may be further purified by means of ion exchange chromatography in order to remove undesired residual ions. Alternatively, if magnesium hydroxide, magnesium carbonate or mixtures thereof have been used to neutralize the fermentation broth, the fermentation broth obtained in process step I) may be acidified to transform the magnesium succinate contained in the medium into the acid form (i. e. succinic acid), which subsequently can be crystallized by cooling down the acidified medium. Examples of further suitable purification processes are disclosed in EP-A-1 005 562, WO-A-2008/010373, WO-A-2011/082378, WO-A-2011/043443, WO-A-2005/030973, WO-A-2011/123268 and WO-A-2011/064151 and EP-A-2 360 137.

According to a preferred embodiment of the process according to the present invention the process further comprises the process step:

III) conversion of the organic compound contained in the fermentation broth obtained in process step I) or conversion of the recovered organic compound obtained in process step II) into a secondary organic product being different from the organic compound by at least one chemical reaction.

In case of succinic acid as the organic compound preferred secondary organic products are selected from the group consisting of succinic acid esters and polymers thereof, tetrahydrofuran (THF), 1,4-butanediol (BDO), gamma-butyrolactone (GBL) and pyrrolidones.

According to a preferred embodiment for the production of THF, BDO and/or GBL this process comprises:
b1) either the direct catalytic hydrogenation of the succinic acid obtained in process steps I) or II) to THF and/or BDO and/or GBL or
b2) the chemical esterification of succinic acid and/or succinic acid salts obtained in process steps I) or II) into its corresponding di-lower alkyl ester and subsequent catalytic hydrogenation of said ester to THF and/or BDO and/or GBL.

According to a preferred embodiment for the production of pyrrolidones this process comprises:
b) the chemical conversion of succinic acid ammonium salts obtained in process steps I) or II) to pyrrolidones in a manner known per se.

For details of preparing these compounds reference is made to US-A-2010/0159543 and WO-A-2010/092155.

A contribution to solving the problems mentioned at the outset is furthermore provided by the use of the modified microorganism according to the present invention for the fermentative production of organic compounds. Preferred organic compounds are those compounds that have already been mentioned in connection with the process according to the present invention, succinic acid being the most preferred organic compound. Furthermore, preferred conditions for the fermentative production of organic compounds, preferably of succinic acid, are those conditions that have already been described in connection with process step I) of the process according to the present invention.

The invention is now explained in more detail with the aid of figures and non-limiting examples.

EXAMPLES

Example 1: General Method for the Transformation of *Basfia succiniciproducens*

TABLE 1

Nomenclature of the DD1-wild-type and mutants referred to in the examples
Strain Wild-type DD1 (deposit DSM18541)
DD1 ΔldhA
DD1 ΔldhA ΔfruA
DD1 ΔldhA ΔpflA
DD1 ΔldhA ΔpflA ΔfruA
DD1 ΔfruA

*Basfia succiniciproducens* DD1 (wild-type) was transformed with DNA by electroporation using the following protocol:

For preparing a pre-culture DD1 was inoculated from frozen stock into 40 ml BHI (brain heart infusion; Becton, Dickinson and Company) in 100 ml shake flask. Incubation was performed over night at 37° C.; 200 rpm. For preparing the main-culture 100 ml BHI were placed in a 250 ml shake flask and inoculated to a final OD (600 nm) of 0.2 with the pre-culture. Incubation was performed at 37° C., 200 rpm. The cells were harvested at an OD of approximately 0.5, 0.6 and 0.7, pellet was washed once with 10% cold glycerol at 4° C. and re-suspended in 2 ml 10% glycerol (4° C.).

100 μl of competent cells were the mixed with 2-8 μg Plasmid-DNA and kept on ice for 2 min in an electroporation cuvette with a width of 0.2 cm. Electroporation under the following conditions: 400Ω; 25 μF; 2.5 kV (Gene Pulser, Bio-Rad). 1 ml of chilled BHI was added immediately after electroporation and incubation was performed for approximately 2 h at 37° C.

Cells were plated on BHI with 5 mg/L chloramphenicol and incubated for 2-5 d at 37° C. until the colonies of the transformants were visible. Clones were isolated and restreaked onto BHI with 5 mg/l chloramphenicol until purity of clones was obtained.

Example 2: Generation of Deletion Constructs

Figure 1:
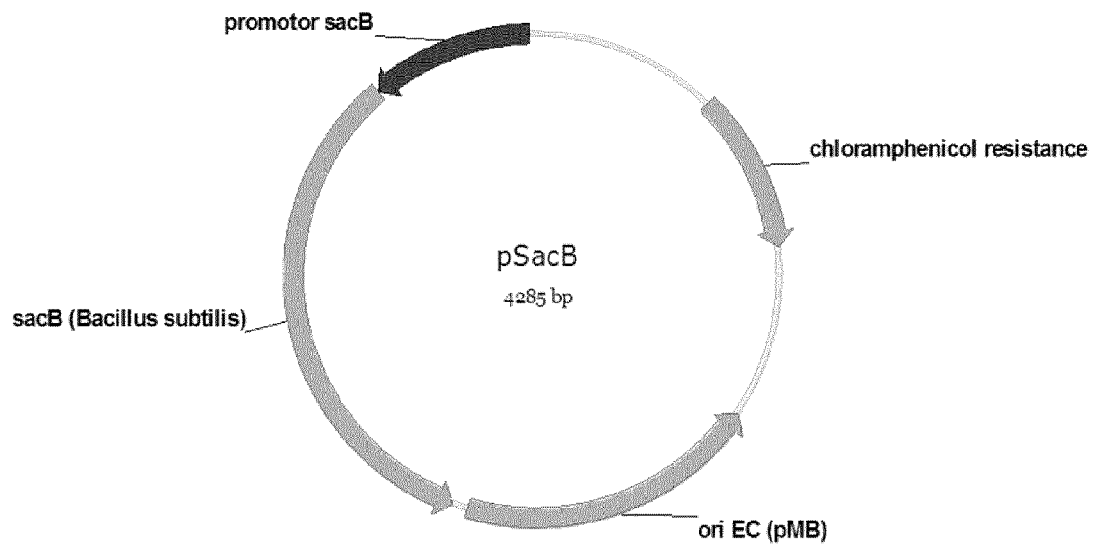
FIG. 1 shows a schematic map of plasmid pSacB (SEQ ID NO: 5).
Figure 2:
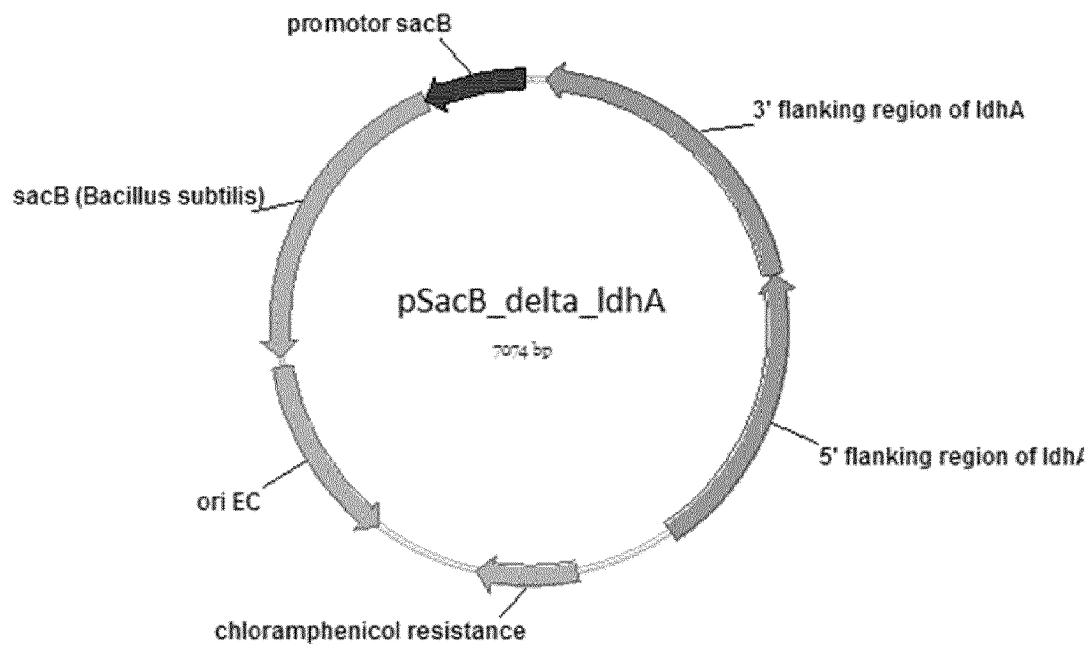
FIG. 2 shows a schematic map of plasmid pSacB ΔldhA (SEQ ID NO: 6).
Figure 3:
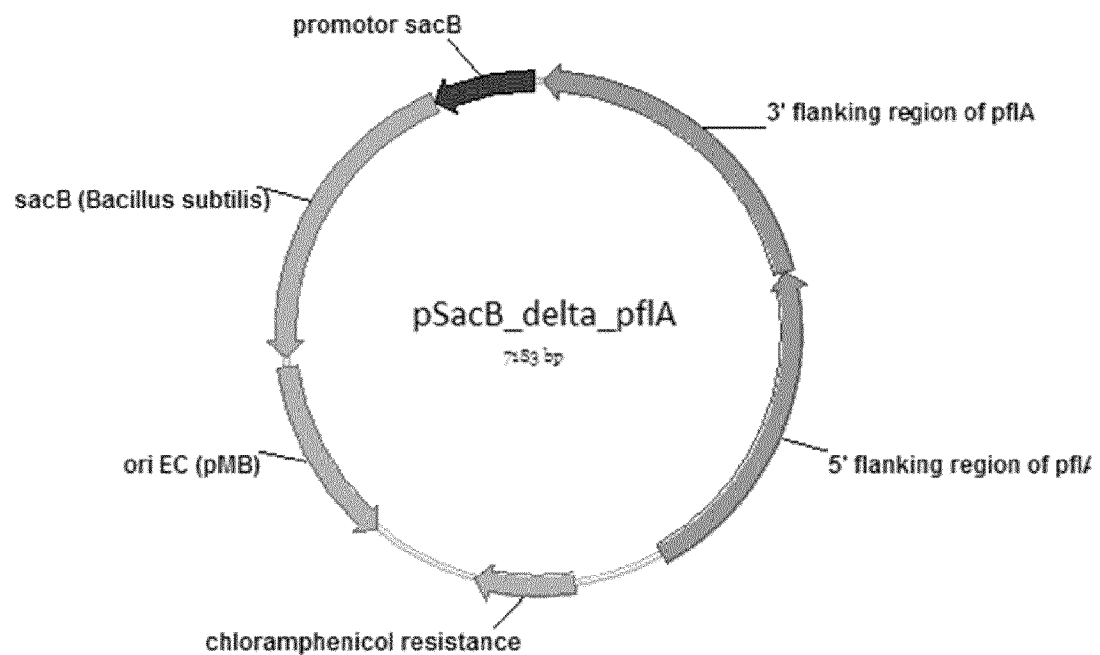
FIG. 3 shows a schematic map of plasmid pSacB ΔpflA (SEQ ID NO: 7).
Figure 4:
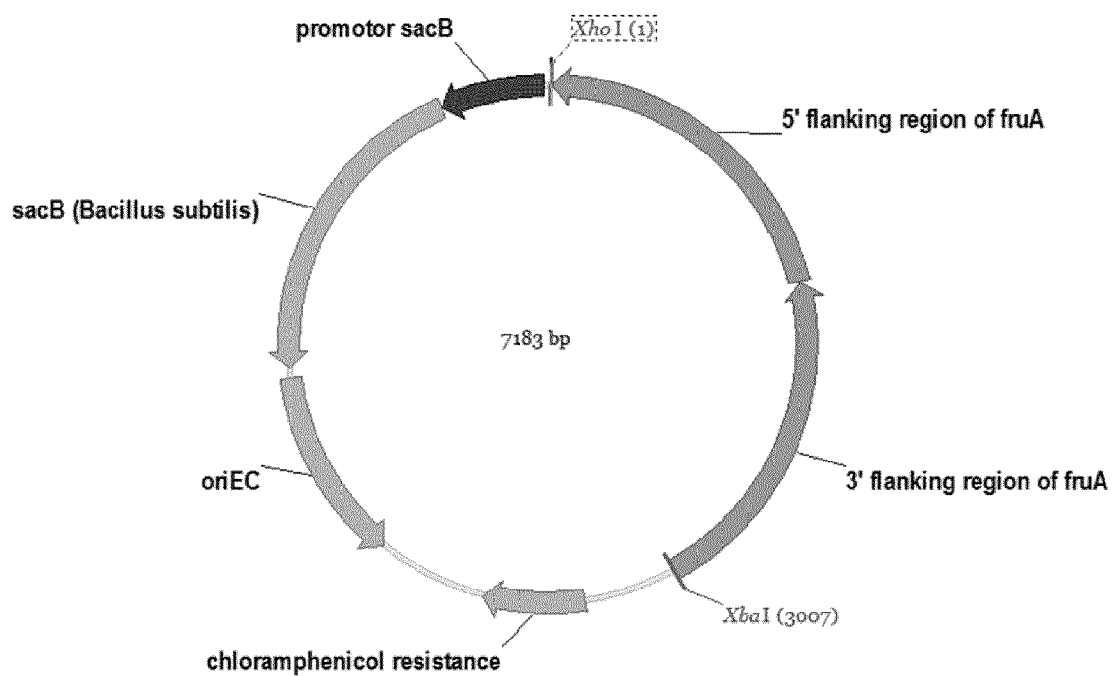
FIG. 4 shows a schematic map of plasmid pSacB ΔfruA (SEQ ID NO: 8).

Mutation/deletion plasmids were constructed based on the vector pSacB (SEQ ID NO: 5). FIG. 1 shows a schematic map of plasmid pSacB. 5'- and 3'-flanking regions (approx. 1500 bp each) of the chromosomal fragment, which should be deleted were amplified by PCR from chromosomal DNA of *Basfia succiniciproducens* and introduced into said vector using standard techniques. Normally, at least 80% of the ORF were targeted for a deletion. In such a way, the deletion plasmids for the lactate dehydrogenase ldhA, pSacB_delta_ldhA (SEQ ID NO: 6), the pyruvate formate lyase activating enzyme pflA, pSacB_delta_pflA (SEQ ID No: 7) and the putative fructose-specific phosphotransferase, fruA, pSacB_delta_fruA (SEQ ID No: 8) were constructed. FIGS. 2, 3 and 4 show schematic maps of plasmid pSacB_delta_ldhA, pSacB_delta_pflA, and pSacB_delta_fruA, respectively.

In the plasmid sequence of pSacB (SEQ ID NO: 5) the sacB-gene is contained from bases 2380-3801. The sacB-promoter is contained from bases 3802-4264. The chloramphenicol gene is contained from base 526-984. The origin of replication for *E. coli* (ori EC) is contained from base 1477-2337 (see FIG. 1).

In the plasmid sequence of pSacB_delta_ldhA (SEQ ID NO: 6) the 5' flanking region of the ldhA-gene, which is homologous to the genome of *Basfia succiniciproducens*, is contained from bases 1519-2850, while the 3' flanking region of the ldhA-gene, which is homologous to the genome of *Basfia succiniciproducens*, is contained from bases 62-1518. The sacB-gene is contained from bases 5169-6590. The sacB-promoter is contained from bases 6591-7053. The chloramphenicol gene is contained from base 3315-3773. The origin of replication for *E. coli* (ori EC) is contained from base 4266-5126 (see FIG. 2).

In the plasmid sequence of pSacB_delta_pflA (SEQ ID NO: 7) the 5' flanking region of the pflA-gene, which is homologous to the genome of *Basfia succiniciproducens*, is contained from bases 1506-3005, while the 3' flanking region of the pflA-gene, which is homologous to the genome of *Basfia succiniciproducens*, is contained from bases 6-1505. The sacB-gene is contained from bases 5278-6699. The sacB-promoter is contained from bases 6700-7162. The chloramphenicol gene is contained from base 3424-3882. The origin of replication for *E. coli* (ori EC) is contained from base 4375-5235 (see FIG. 3).

In the plasmid sequence of pSacB_delta_fruA (SEQ ID NO: 8) the 3' flanking region of the fruA-gene, which is homologous to the genome of *Basfia succiniciproducens*, is contained from bases 1506-3005, while the 5' flanking region of the fruA-gene, which is homologous to the genome of *Basfia succiniciproducens*, is contained from bases 6-1505. The sacB-gene is contained from bases 5278-6699. The sacB-promoter is contained from bases 6700-7162. The chloramphenicol gene is contained from base 3424-3882. The origin of replication for *E. coli* (ori EC) is contained from base 4375-5235 (see FIG. 4).

Example 3: Generation of Improved Succinate Producing Strains a) *Basfia succiniciproducens* DD1 was transformed as described above with the pSacB_delta_ldhA and "Campbelled in" to yield a "Campbell in" strain. Transformation and integration into the genome of *Basfia succiniciproducens* was confirmed by PCR yielding bands for the integrational event of the plasmid into the genome of *Basfia* succiniciproducens.

The "Campbell in" strain was then "Campbelled out" using agar plates containing sucrose as a counter selection medium, selecting for the loss (of function) of the sacB gene. Therefore, the "Campbell in" strains were incubated in 25-35 ml of non selective medium (BHI containing no antibiotic) at 37° C., 220 rpm over night.

The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB-levan-sucrase gene onto sucrose and growth medium containing agar plates for the purpose of selecting for strains with the loss of the sacB gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies.

The "Campbelled out" strains containing either the wild-type situation of the ldhA-locus or the mutation/deletion of the ldhA-gene were confirmed by chloramphenicol sensitivity. The mutation/deletion mutants among these strains were identified and confirmed by PCR analysis. This led to the ldhA-deletion mutant *Basfia succiniciproducens* DD1 ΔldhA.

b) *Basfia succiniciproducens* DD1 ΔldhA was transformed with pSacB_delta_pflA as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflA-double deletion mutant *Basfia succiniciproducens* DD1 ΔldhA ΔpflA.

c) *Basfia succiniciproducens* DD1 ΔldhA ΔpflA was transformed with pSacB_delta_fruA as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflD fruA-triple deletion mutant *Basfia succiniciproducens* DD1 ΔldhA ΔpflA ΔfruA.

d) *Basfia succiniciproducens* DD1 was transformed with pSacB_delta_fruA as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the fruA-deletion mutant *Basfia succiniciproducens* DD1 ΔfruA.

Example 4: Cultivation of DD1 and DD1 ΔfruA on Sucrose

The productivity of the DD1-strain was compared with the productivity of the mutant strain DD1 ΔfruA in the presence of sucrose as a carbon source.

Productivity was analyzed utilizing media and incubation conditions described below.

1. Medium Preparation

The composition and preparation of the cultivation medium is as described in the following table 2 (Medium CGM), 3 (trace element solution 1), 4 (of vitamin solution 1) and 5 (Medium LSM_1).

TABLE 2

Medium composition for cultivation on glucose (medium CGM)

| Compound | Concentration [g/L] |
|---|---|
| Yeast extract (Bio Springer) | 10.0 |
| $CaCl_2 \times 2H_2O$ | 0.2 |
| $MgCl_2 \times 6H_2O$ | 0.2 |
| $(NH_4)_2SO_4$ | 2.0 |
| NaCl | 1.0 |
| $K_2HPO_4$ | 3.0 |
| $MgCO_3$ | 50.0 |
| $NaHCO_3$ | 8.4 |
| glucose | 52 |

TABLE 3

Composition of trace element solution 1.
Trace element solution

| Compound | Final concentration |
|---|---|
| citric acid | 10 g/L |
| $ZnSO_4 \times 7H_2O$ | 1851 mg/L |
| $CaSO_4 \times 2H_2O$ | 10 mg/L |
| $FeSO_4 \times 7H_2O$ | 2040 mg/L |
| $CaCl_2 \times 2H_2O$ | 12460 mg/L |
| $MnCl_2 \times 4H_2O$ | 1200 mg/L |
| $Na_2MoO_4 \times 2H_2O$ | 38 mg/L |
| $CuCl_2 \times 2H_2O$ | 188 mg/L |
| $NiCl_2 \times 6H_2O$ | 32 mg/L |
| $CoCl_2 \times 6H_2O$ | 101 mg/L |

TABLE 4

Composition of vitamin solution 1
Vitamin solution

| Compound | Final concentration |
|---|---|
| Thiamin HCl (B1) | 1.0 g/L |
| Nicotinic acid (B3) | 1.0 g/L |
| Riboflavin (B2) | 20 mg/L |
| Biotin (B7) | 50 mg/L |
| Pantothenic acid (B5) | 1.0 g/L |
| Pyridoxine (B6) | 1.0 g/L |
| Cyanocobalamin (B12) | 50 mg/L |
| Lipoic acid | 5 mg/L |

TABLE 5

Composition of LSM_1 medium for cultivation on sucrose.

| Compound | Volume/Mass | Stock concentration | Final concentration |
|---|---|---|---|
| Medium 1 | | | |
| $MgCO_3$ | 2.5 g | 100% | 50.00 g/L |
| Water | 38.45 mL | — | — |
| Medium 2 | | | |
| Succinic acid | 2.5 mL | 50 g/L | 2.50 g/L |
| Sucrose | 4.00 mL | 650 g/L | 52.00 g/L |
| $(NH_4)_2SO_4$ | 0.5 mL | 500 g/L | 5.00 g/L |
| Betain | 0.5 mL | 23 g/L | 0.23 g/L |
| $KH_2PO_4$ | 0.50 mL | 100 g/L | 1.00 g/L |
| $Na_2CO_3$ | 0.50 mL | 200 g/L | 2.00 g/L |
| vitamin solution 1 | 0.50 mL | 4 g/L | 0.04 g/L |

TABLE 5-continued

Composition of LSM_1 medium for cultivation on sucrose.

| Compound | Volume/Mass | Stock concentration | Final concentration |
|---|---|---|---|
| trace element solution 1 | 0.05 mL | 21 g/L | 0.02 g/L |

2. Cultivations and Analytics

For growing the pre-culture bacteria from a freshly grown BHI-agar plate (incubated overnight at 37° C. under anaerobic conditions) was used to inoculate to OD600=0.75 a 100 ml-serum bottle with gas tight butyl rubber stopper containing 50 ml of the CGM liquid medium described in table 2 with a $CO_2$-atmosphere. The bottles were incubated at 37° C. and 170 rpm (shaking diameter: 2.5 cm). For growing the main culture 2.5 ml of the bacterial culture in the CGM medium (after 11 hours of incubation) was used to inoculate a 100 ml-serum bottle with gas tight butyl rubber stopper containing 50 ml of the LSM_1 liquid medium described in table 5 with a $CO_2$-atmosphere. Consumption of sucrose and production of carboxylic acids was quantified via HPLC (HPLC methods are described in tables 13 and 14) after 24 h. Cell growth was measured by measuring the absorbance at 600 nm (OD600) using a spectrophotometer (Ultrospec3000, Amersham Biosciences, Uppsala Sweden).

3. Results

The results of the cultivation experiments with DD1 and DD1 ΔfruA are shown in table 6. The deletion of fruA resulted on sucrose in a significant enhanced succinic acid concentration and an enhanced carbon yield of succinic acid.

TABLE 6

Cultivation of the DD1-strain and the DD1 ΔfruA-strain on sucrose

| | DD1 | DD1 ΔfruA |
|---|---|---|
| substrate | sucrose | sucrose |
| tc [h]$^a$ | 24 | 24 |
| $\Delta C_{Sucrose}$ [g/l]$^b$ | 51.8 | 51.8 |
| $\Delta C_{SA}$[g/l]$^{c}$ (succinic acid) | 24.67 | 33.86 |
| $\Delta C_{LA}$ [g/L]$^{c,h}$ (lactic acid) | 8.20 | 1.24 |
| $\Delta C_{FA}$[g/l]$^{c,h}$ (formic acid) | 7.73 | 4.11 |
| $\Delta C_{AA}$[g/l]$^{c,h}$ (acetic acid) | 8.92 | 9.21 |
| $\Delta C_{PA}$[g/l]$^{c,h}$ (pyruvic acid) | 0.11 | 0.00 |
| $\Delta C_{E}$[g/l]$^{c}$ (ethanol) | 0.00 | 0.00 |
| SA Yield (SA/S) [g/g]$^{g}$ | 0.48 | 0.65 |

$^a$cultivation time
$^b$consumption of substrate (sucrose)
$^c$formation of succinic acid, lactic acid, formic acid, acetic acid, pyruvic acid and ethanol
$^g$SA yield (ration of SA per consumed substrate)
$^h$detection limits for acetic acid, lactic acid, malic acid, and formic acid were found to be lower than 0.01 g/l in the given HPLC method Example 5: Cultivation of DD1 ΔldhA and DD1 ΔldhA ΔfruA on Sucrose The productivity of the DD1 ΔldhA-strain was compared with the productivity of the mutant strain DD1 ΔldhA ΔfruA in the presence sucrose as a carbon source.

Productivity was analyzed utilizing media and incubation conditions described below.

1. Medium Preparation

The composition and preparation of the cultivation medium (Medium P) is as described in the following table 7.

TABLE 7

Composition of Medium P for cultivation on sucrose.

| Compound | Volume/Mass | Stock concentration | Final concentration |
|---|---|---|---|
| Medium 1 | | | |
| $MgCO_3$ | 2.5 g | 100% | 50.00 g/L |
| Water | 28 mL | — | — |
| Medium 2 | | | |
| Yeast extract | 5.00 mL | 100 g/L | 10.00 g/L |
| Sucrose | 3.85 mL | 650 g/L | 50.00 g/L |
| $(NH_4)_2SO_4$ | 0.20 mL | 500 g/L | 2.00 g/L |
| $K_2HPO_4$ | 1.50 mL | 100 g/L | 3.00 g/L |
| $NaHCO_3$ | 5.60 mL | 75 g/L | 8.40 g/L |
| NaCl | 0.25 mL | 200 g/L | 1.00 g/L |
| $MgCl_2 \times 6H_2O$ | 0.20 mL | 50 g/L | 0.20 g/L |
| $CaCl_2 \times 2H_2O$ | 0.20 mL | 50 g/L | 0.20 g/L |

2. Cultivations and Analytics

For growing the main culture bacteria from a freshly grown BHI-agar plate (incubated overnight at 37° C. under anaerobic conditions) was used to inoculate to OD600=0.75 a 100 ml-serum bottle with gas tight butyl rubber stopper containing 50 ml of the liquid medium (Medium P) described in table 7 with a $CO_2$-atmosphere. The bottles were incubated at 37° C. and 170 rpm (shaking diameter: 2.5 cm). Consumption of sucrose and production of carboxylic acids was quantified via HPLC (HPLC methods are described in tables 13 and 14) after 24 h. Cell growth was measured by measuring the absorbance at 600 nm (OD600) using a spectrophotometer (Ultrospec3000, Amersham Biosciences, Uppsala Sweden).

3. Results

The results of the cultivation experiments with DD1 ΔldhA and DD1 ΔldhA ΔfruA are shown in table 8. The deletion of fruA resulted on sucrose in a significant enhanced succinic acid concentration and an enhanced carbon yield of succinic acid.

TABLE 8

Cultivation of the DD1 ΔldhA ΔpflA-strain and the DD1 ΔldhA ΔpflA ΔfruA-strain on sucrose

| | DD1 ΔldhA | DD1 ΔldhA ΔfruA |
|---|---|---|
| substrate | sucrose | sucrose |
| tc [h]$^a$ | 24 h | 24 h |
| $\Delta C_{Sucrose}$ [g/l]$^b$ | 51.10 | 51.10 |
| $\Delta C_{SA}$[g/l]$^{c}$ (succinic acid) | 26.92 | 30.53 |
| $\Delta C_{LA}$ [g/L]$^{c,h}$ (lactic acid) | 0.31 | 0.23 |
| $\Delta C_{FA}$[g/l]$^{c,h}$ (formic acid) | 7.70 | 8.53 |
| $\Delta C_{AA}$[g/l]$^{c,h}$ (acetic acid) | 8.40 | 10.53 |
| $\Delta C_{PA}$[g/l]$^{c,h}$ (pyruvic acid) | 2.01 | 1.45 |
| $\Delta C_{E}$[g/l]$^{c}$ (ethanol) | 0.95 | 0.53 |
| SA Yield (SA/S) [g/g]$^{g}$ | 0.53 | 0.60 |

$^a$cultivation time
$^b$consumption of substrate (sucrose)
$^c$formation of succinic acid, lactic acid, formic acid, acetic acid, pyruvic acid and ethanol
$^g$SA yield (ration of SA per consumed substrate)
$^h$detection limits for acetic acid, lactic acid, malic acid, and formic acid were found to be lower than 0.01 g/l in the given HPLC method Example 6: Cultivation of DD1 ΔldhA ΔpflA and DD1 ΔldhA ΔpflA ΔfruA on Sucrose The productivity of the DD1 ΔldhA ΔpflA-strain was compared with the productivity of the mutant strain DD1 ΔldhA ΔpflA ΔfruA in the presence sucrose as a carbon source.

Productivity was analyzed utilizing media and incubation conditions described below.

1. Medium Preparation

The composition and preparation of the cultivation medium (LSM_2) is as described in the following table 9, 10 and 11.

TABLE 9

Composition of trace element solution 2.
Trace element solution

| Compound | Final concentration |
|---|---|
| citric acid | 3.5 g/L |
| $ZnSO_4 \times 7H_2O$ | 1851 mg/L |
| $CaSO_4 \times 2H_2O$ | 10 mg/L |
| $FeSO_4 \times 7H_2O$ | 2040 mg/L |
| $CaCl_2 \times 2H_2O$ | 12460 mg/L |
| $MnCl_2 \times 4H_2O$ | 1200 mg/L |
| $Na_2MoO_4 \times 2H_2O$ | 38 mg/L |
| $CuCl_2 \times 2H_2O$ | 188 mg/L |
| $NiCl_2 \times 6H_2O$ | 32 mg/L |
| $CoCl_2 \times 6H_2O$ | 101 mg/L |

TABLE 10

Composition of vitamin solution 2.
Vitamin solution

| Compound | Final concentration |
|---|---|
| Thiamin HCl (B1) | 500 mg/L |
| Nicotinic acid (B3) | 500 mg/L |
| Riboflavin (B2) | 20 mg/L |
| Biotin (B7) | 5 mg/L |
| Pantothenic acid (B5) | 100 mg/L |
| Pyridoxine (B6) | 500 mg/L |
| Cyanocobalamin (B12) | 5 mg/L |
| Lipoic acid | 5 mg/L |

TABLE 11

Composition of LSM_2 medium for cultivation on sucrose.

| Compound | Volume/Mass | Stock concentration | Final concentration |
|---|---|---|---|
| Medium 1 | | | |
| $MgCO_3$ | 2.5 g | 100% | 50.00 g/L |
| Water | 28 mL | — | — |
| Medium 2 | | | |
| Succinic acid | 2.5 mL | 50 g/L | 2.50 g/L |
| Sucrose | 3.85 mL | 650 g/L | 50.00 g/L |
| $(NH_4)_2SO_4$ | 0.25 mL | 500 g/L | 2.50 g/L |
| $(NH_4)_2HPO_4$ | 0.50 mL | 200 g/L | 2.00 g/L |
| $K_2CO_3$ | 0.50 mL | 200 g/L | 2.00 g/L |
| $KH_2PO_4$ | 0.50 mL | 100 g/L | 1.00 g/L |
| $Na_2CO_3$ | 0.50 mL | 200 g/L | 2.00 g/L |
| vitamin solution 2 | 0.50 mL | 25 g/L | 0.25 g/L |
| trace element solution 2 | 0.50 mL | 21 g/L | 0.21 g/L |

2. Cultivations and Analytics

For growing the main culture bacteria from a freshly grown BHI-agar plate (incubated overnight at 37° C. under anaerobic conditions) was used to inoculate to OD600=0.75 a 100 ml-serum bottle with gas tight butyl rubber stopper containing 50 ml of the liquid medium LSM_2 described in table 11 with a $CO_2$-atmosphere. The bottles were incubated at 37° C. and 160 rpm (shaking diameter: 2.5 cm). Consumption of sucrose and production of carboxylic acids was quantified via HPLC (HPLC methods are described in tables 13 and 14) after 24 h. Cell growth was measured by measuring the absorbance at 600 nm (OD600) using a spectrophotometer (Ultrospec3000, Amersham Biosciences, Uppsala Sweden).

3. Results

The results of the cultivation experiments with DD1 ΔldhA ΔpflA and DD1 ΔldhA ΔpflA ΔfruA are shown in table 12. The deletion of fruA resulted on sucrose in a significant enhanced succinic acid concentration and an enhanced carbon yield of succinic acid.

TABLE 12

Cultivation of the DD1 ΔldhA ΔpflA-strain and the
DD1 ΔldhA ΔpflA ΔfruA-strain on sucrose

| | DD1 ΔldhA ΔpflA | DD1 ΔldhA ΔpflA ΔfruA |
|---|---|---|
| substrate | sucrose | sucrose |
| tc [h]$^a$ | 24 h | 24 h |
| $\Delta C_{Sucrose}$ [g/l]$^b$ | 52.50 | 52.50 |
| $\Delta C_{SA}$ [g/l]$^c$ (succinic acid) | 30.29 | 34.76 |
| $\Delta C_{LA}$ [g/L]$^{c,h}$ (lactic acid) | 0.19 | 0.18 |
| $\Delta C_{FA}$ [g/l]$^{c,h}$ (formic acid) | 0.00 | 0.00 |
| $\Delta C_{AA}$ [g/l]$^{c,h}$ (acetic acid) | 2.29 | 3.72 |
| $\Delta C_{PA}$ [g/l]$^{c,h}$ (pyruvic acid) | 2.29 | 1.74 |
| $\Delta C_E$ [g/l]$^c$ (ethanol) | 0.00 | 0.00 |
| SA Yield (SA/S) [g/g]$^g$ | 0.58 | 0.66 |

$^a$cultivation time
$^b$consumption of substrate (sucrose)
$^c$formation of succinic acid, lactic acid, formic acid, acetic acid, pyruvic acid and ethanol
$^g$SA yield (ration of SA per consumed substrate)
$^h$detection limits for acetic acid, lactic acid, malic acid, and formic acid were found to be lower than 0.01 g/l in the given HPLC method

TABLE 13

HPLC method (ZX-THF50) for analysis of succinic acid, formic acid, lactic acid, acetic acid, pyruvic acid and ethanol

| HPLC column | Aminex HPX-87 H, 300 × 7.8 mm (BioRad) |
|---|---|
| Precolumn | Cation H |
| Temperature | 50° C. |
| Eluent flow rate | 0.50 ml/min |
| Injection volume | 5.0 μl |
| Diode array detector | RI-Detector |
| Runtime | 28 min |
| max. pressure | 140 bar |
| Eluent A | 5 mM $H_2SO_4$ |
| Eluent B | 5 mM $H_2SO_4$ |

| | Time [min] | A [%] | B [%] | Flow [ml/min] |
|---|---|---|---|---|
| Gradient | 0.0 | 50 | 50 | 0.50 |
| | 28.0 | 50 | 50 | 0.50 |

TABLE 14

HPLC method (Fast-CH) for analysis of sucrose

| HPLC column | Fast Carbohydrate, 100 × 7.8 mm (Biorad) |
|---|---|
| Precolumn | Deashing Refill Cartridges (30° C.) |
| Temperature | 75° C. |
| Eluent flow rate | 1.00 ml/min |
| Injection volume | 1.0 μl |
| Diode array detector | RI-Detector |
| Runtime | 8 min |
| max. pressure | 150 bar |
| Eluent A | water |
| Eluent B | water |

| | Time [min] | A [%] | B [%] | Flow [ml/min] |
|---|---|---|---|---|
| Gradient | 0.0 | 50 | 50 | 1.00 |
| | 8.0 | 50 | 50 | 1.00 |

The invention claimed is:

1. A method of producing succinic acid comprising
I) cultivating a modified microorganism in a culture medium comprising sucrose as an assimilable carbon source to allow the modified microorganism to produce succinic acid, thereby obtaining a fermentation broth comprising succinic acid, wherein the modified microorganism is a modified bacterial cell of the genus *Basfia* in which the fruA-gene or at least a part thereof has been deleted;
II) recovering succinic acid from the fermentation broth obtained in process step I);
wherein the assimilable carbon source is not a mixture of glycerol and sucrose and wherein at least 95 wt.-% of the assimilable carbon source, based on the total weight of the assimilable carbon source with the exception of carbon dioxide, is sucrose.

2. The method according to claim 1, wherein the modified microorganism has a 16S rDNA of SEQ ID NO: 1 or a sequence, which shows a sequence homology of at least 96, 97, 98, 99 or 99.9% with SEQ ID NO: 1.

3. The method according to claim 1, wherein the modified microorganism belongs to the species *Basfia succiniciproducens*.

4. The method according to claim 1, wherein the fruA-gene comprises a nucleic acid selected from the group consisting of:
   a) nucleic acids having the nucleotide sequence of SEQ ID NO: 3;
   b) nucleic acids encoding the amino acid sequence of SEQ ID NO: 4;
   c) nucleic acids which are at least 70% identical to the nucleic acid of a) or b), the identity being the identity over the total length of the nucleic acids of a) or b);
   d) nucleic acids encoding an amino acid sequence which is at least 70% identical to the amino acid sequence encoded by the nucleic acid of a) or b), the identity being the identity over the total length of amino acid sequence encoded by the nucleic acids of a) orb);
   e) nucleic acids capable of hybridizing under stringent conditions with a complementary sequence of any of the nucleic acids according to a) or b); and
   f) nucleic acids encoding the same protein as any of the nucleic acids of a) or b), but differing from the nucleic acids of a) or b) above due to the degeneracy of the genetic code.

5. The method according to claim 1, wherein the modified microorganism comprises:
   A) a deletion of the ldhA-gene or at least a part thereof, a deletion of a regulatory element of the ldhA-gene or at least a part thereof or an introduction of at least one mutation into the ldhA-gene;
   B) a deletion of the pflD-gene or at least a part thereof, a deletion of a regulatory element of the pflD-gene or at least a part thereof or an introduction of at least one mutation into the pflD-gene;
   C) a deletion of the pflA-gene or at least a part thereof, a deletion of a regulatory element of the pflA-gene or at least a part thereof or an introduction of at least one mutation into the pflA-gene;
   D) a deletion of the ldhA-gene or at least a part thereof, a deletion of a regulatory element of the ldhA-gene or at least a part thereof or an introduction of at least one mutation into the ldhA-gene
   and
   a deletion of the pflD-gene or at least a part thereof, a deletion of a regulatory element of the pflD-gene or at least a part thereof or an introduction of at least one mutation into the pflD-gene;
   or
   E) a deletion of the ldhA-gene or at least a part thereof, a deletion of a regulatory element of the ldhA-gene or at least a part thereof or an introduction of at least one mutation into the ldhA-gene
   and
   a deletion of the pflA-gene or at least a part thereof, a deletion of a regulatory element of the pflA-gene or at least a part thereof or an introduction of at least one mutation into the pflA-gene.

6. The method according to claim 1, wherein the process further comprises the process step:
   III) conversion of succinic acid contained in the fermentation broth obtained in process step I) or conversion of the recovered succinic acid obtained in process step II) into a secondary organic product being different from succinic acid by at least one chemical reaction.

7. The method according to claim 6, wherein the secondary organic product is selected from the group consisting of succinic acid esters or polymers thereof, tetrahydrofuran (THF), 1,4-butanediol (BDO), gamma-butyrolactone (GBL) and pyrrolidones.

* * * * *